(12) United States Patent
Haydar et al.

(10) Patent No.: US 8,063,053 B2
(45) Date of Patent: Nov. 22, 2011

(54) 1-(ARYLSULFONYL)-4-(PIPERAZIN-1-YL)-1H-BENZIMIDAZOLES AS 5-HYDROXYTRYPTAMINE-6 LIGANDS

(75) Inventors: Simon Nicolas Haydar, Newtown, PA (US); Patrick Michael Andrae, Jamesburg, NJ (US); Heedong Yun, Tenafly, NJ (US); Albert Jean Robichaud, Ringoes, NJ (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 12/616,201

(22) Filed: Nov. 11, 2009

(65) Prior Publication Data
US 2010/0120779 A1 May 13, 2010

Related U.S. Application Data

(60) Provisional application No. 61/113,296, filed on Nov. 11, 2008.

(51) Int. Cl.
| | |
|---|---|
| A61K 31/496 | (2006.01) |
| C07D 235/06 | (2006.01) |
| C07D 235/08 | (2006.01) |
| A61K 31/407 | (2006.01) |
| C07D 487/08 | (2006.01) |

(52) U.S. Cl. .................. 514/254.06; 514/407; 544/370; 548/305.1

(58) Field of Classification Search ........................ None
See application file for complete search history.

(56) References Cited

U.S. PATENT DOCUMENTS

| | | | |
|---|---|---|---|
| 5,849,759 A | 12/1998 | Arnaiz et al. | |
| 5,990,105 A | 11/1999 | Bos et al. | |
| 6,251,893 B1 | 6/2001 | Maddaford et al. | |
| 6,255,306 B1 | 7/2001 | Macor | |
| 6,288,103 B1 | 9/2001 | Faull et al. | |
| 6,316,450 B1 | 11/2001 | Bromidge et al. | |
| 6,380,199 B1 | 4/2002 | Reavill et al. ............ | 514/252.13 |
| 6,423,717 B1 | 7/2002 | Bromidge et al. | |
| 6,559,167 B1 | 5/2003 | Garst et al. | |
| 7,034,029 B2 | 4/2006 | Kelly et al. | |
| 7,087,750 B2 | 8/2006 | Caldirola et al. | |
| 7,282,495 B2 | 10/2007 | Kelly et al. | |
| 2002/0165251 A1 | 11/2002 | Caldirola et al. | |
| 2004/0192749 A1 | 9/2004 | Kelly et al. | |
| 2006/0069094 A1 | 3/2006 | Bonhaus et al. | |

FOREIGN PATENT DOCUMENTS

| | | |
|---|---|---|
| EP | 0930302 | 7/1999 |
| WO | 9603400 | 2/1996 |
| WO | 9827081 | 6/1998 |
| WO | 9902502 | 1/1999 |
| WO | 9965906 | 12/1999 |
| WO | 0208178 | 1/2002 |
| WO | 0232863 | 4/2002 |
| WO | WO 02/36562 A2 | 5/2002 |
| WO | WO 02/102774 A1 | 12/2002 |
| WO | WO 03/026664 A1 | 4/2003 |
| WO | WO 2004/035740 A2 | 4/2004 |
| WO | WO 2005/112938 A2 | 12/2005 |
| WO | WO 2006/015259 A2 | 2/2006 |

OTHER PUBLICATIONS

Robichaud et al. In Annual Reports in Medicinal Chemistry, vol. 36, p. 11-20 (2000).*
Rogers et al. Psychopharmacology, vol. 158, p. 114-119 (2001).*
Mahmood et al., "Bicyclic heteroarylpiperazines as selective brain penetrant 5-HT$_6$ receptor antagonists" *Bioorganic & Medicinal Chemistry Letters* vol. 15, No. 21 (2005) pp. 4867-4871.
Holenz et al., "Medicinal chemistry strategies to 5-HT$_6$ receptor ligands as potential cognitive enhancers and antiobesity agents" *Drug Discovery Today* vol. 11 No. 7-8 (2006) pp. 283-299.
Holenz, J., et al., "Medicinal Chemistry Strategies to 5-HT$_6$ Receptor Ligands as Potential Cognitive Enhancer and Antiobesity Agents", Drug Discovery Today, 2006, pp. 283-299, vol. 11, Appendix 1.
Routledge, C., et al., "Characterization of SB-271046: A Potent, Selective and Orally Active 5-HT$_6$ Receptor Antagonist", British Journal of Pharmacology, 2000, pp. 1606-1612, vol. 130, Appendix 2.
Mitchell, E., et al., "5-HT$_6$ Receptors: A Novel Target for Cognitive Enhancements", Pharmacology & Therapeutics, 2005, pp. 320-333, vol. 108, Appendix 3.
Schechter, L. E., et al., "Neuropharmacological Profile of Novel and Selective 5-HT$_6$ Receptor Agonists: WAY-181187 and WAY-208466", Neuropsychopharmacology, 2008, pp. 1323-1335, vol. 33, Appendix 4.

(Continued)

*Primary Examiner* — Emily Bernhardt
(74) *Attorney, Agent, or Firm* — Jennifer A. Kispert

(57) ABSTRACT

The invention relates to 1-(arylsulfonyl)-4-(piperazin-1-yl)-1H-benzimidazole compounds of the Formula I:

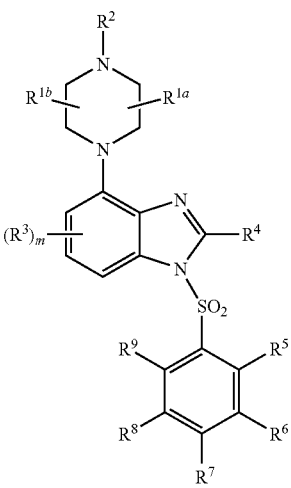

or a tautomer, stereoisomer, or pharmaceutically acceptable salt thereof, wherein the constituent variables are as defined herein, compositions comprising the compounds, and methods for making and using the compounds.

18 Claims, No Drawings

OTHER PUBLICATIONS

Pullagurla, M., et al., "Modulation of the Stimulus Effects of (+) amphetamine by the 5-HT6 Antagonist MS-245", Pharmacology, Biochemistry and Behavior, 2004, pp. 263-268, vol. 78, Appendix 5.

Messina, et al., "Association of the 5-$HT_6$ Receptor Gene Polymorphism C267T with Parkinson's Disease", Neurology, 2002, pp. 828-829, vol. 58, Appendix 6.

Ernst, M., et al., "DOPA Decarboxylase Activity in Attention Deficit Hyperactivity Disorder Adults. A [Fluorine-18]Fluorodopa Positron Emission Tomographic Study", The Journal of Neuroscience, 1998, pp. 5901-5907, vol. 18, Appendix 8.

CAS STN Registry entry No. 1028268-34-9; entered Jun. 15, 2008.
CAS STN Registry entry No. 1027325-53-6; entered Jun. 11, 2008.
CAS STN Registry entry No. 1027222-67-8; entered Jun. 11, 2008.
CAS STN Registry entry No. 1026749-96-1; entered Jun. 9, 2008.
CAS STN Registry entry No. 1025813-79-9; entered Jun. 5, 2008.
Chalmers, et al., TiPs, vol. 17, pp. 166-172, (Apr. 1996).
Methvin, Isaac et al., Bioorganic & Medicinal Chemistry Letters, vol. 10, pp. 1719-1721, (2000).
Russell, M.G., et al., Curr. Top. Med. Chem., vol. 2, No. 6, pp. 643-654, (Jun. 2002).

* cited by examiner

1-(ARYLSULFONYL)-4-(PIPERAZIN-1-YL)-1H-BENZIMIDAZOLES AS 5-HYDROXYTRYPTAMINE-6 LIGANDS

FIELD OF THE INVENTION

The present invention is directed to 1-(arylsulfonyl)-4-(piperazin-1-yl)-1H-benzimidazole compounds, pharmaceutical compositions processes for their preparation, their use for modulation of $5\text{-HT}_6$ activity and methods for treatment of central nervous system (CNS) disorders.

BACKGROUND OF THE INVENTION

Serotonin (5-hydroxytryptamine) (5-HT) receptors play a critical role in many physiological and behavioral functions in humans and animals. These functions are mediated through various 5-HT receptors distributed throughout the body. There are now approximately fifteen different human 5-HT receptor subtypes that have been cloned, many with well-defined roles in humans. A recently identified 5-HT receptor subtype is the $5\text{-HT}_6$ receptor, first cloned from rat tissue in 1993 (Monsma, F. J.; Shen, Y.; Ward, R. P.; Hamblin, M. W. *Molecular Pharmacology* 1993, 43, 320-327) and subsequently from human tissue (Kohen, R.; Metcalf, M. A.; Khan, N.; Druck, T.; Huebner, K.; Sibley, D. R. *Journal of Neurochemistry* 1996, 66, 47-56). The receptor is a G-protein coupled receptor (GPCR) positively coupled to adenylate cyclase (Ruat, M., Traiffort, E., Arrang, J-M., Tardivel-Lacombe, L., Diaz, L., Leurs, R., and Schwartz, J.-C., *Biochemical Biophysical Research Communications* 1993, 193, 268-276). The receptor is found almost exclusively in the central nervous system (CNS) areas both in rat and in human. In situ hybridization studies of the $5\text{-HT}_6$ receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

$5\text{-HT}_6$ receptor in rat brain using mRNA indicate principal localization in the areas of 5-HT projection including striatum, nucleus accumbens, olfactory tubercle, and hippocampal formation (Ward, R. P.; Hamblin, M. W.; Lachowicz, J. E.; Hoffman, B. J.; Sibley, D. R.; Dorsa, D. M. *Neuroscience* 1995, 64, 1105-1111).

There are many potential therapeutic uses for $5\text{-HT}_6$ ligands in humans based on direct effects and on indications from available scientific studies. These studies include the localization of the receptor, the affinity of ligands with known in vivo activity, and various animal studies conducted so far.

One potential therapeutic use of modulators of $5\text{-HT}_6$ receptor function is in the enhancement of cognition and memory in human diseases such as Alzheimer's. The high levels of receptor found in important structures in the forebrain, including the caudate/putamen, hippocampus, nucleus accumbens, and cortex suggest a role for the receptor in memory and cognition since these areas are known to play a vital role in memory (Gerard, C.; Martres, M.-P.; Lefevre, K.; Miguel, M. C.; Verge, D.; Lanfumey, R.; Doucet, E.; Hamon, M.; E I Mestikawy, S. *Brain Research*, 1997, 746, 207-219). The ability of known $5\text{-HT}_6$ receptor ligands to enhance cholinergic transmission also supported the potential cognition use (Bentley, J. C.; Boursson, A.; Boess, F. G.; Kone, F. C.; Marsden, C. A.; Petit, N.; Sleight, A. J. *British Journal of Pharmacology*, 1999, 126(7), 1537-1542). Studies have found that a known $5\text{-HT}_6$ selective antagonist significantly increased glutamate and aspartate levels in the frontal cortex without elevating levels of noradrenaline, dopamine, or 5-HT. This selective elevation of neurochemicals known to be involved in memory and cognition point to a role for $5\text{-HT}_6$ ligands in cognition (Dawson, L. A.; Nguyen, H. Q.; Li, P. *British Journal of Pharmacology*, 2000, 130(1), 23-26). Animal studies of memory and learning with a known selective $5\text{-HT}_6$ antagonist found positive effects (Rogers, D. C.; Hatcher, P. D.; Hagan, J. J. *Society of Neuroscience, Abstracts* 2000, 26, 680).

A related potential therapeutic use for $5\text{-HT}_6$ ligands, particularly antagonists, is the treatment of attention deficit disorders (ADD) and Attention Deficit Hyperactivity Disorder (ADHD) in both children and adults. Ernst, M; Zametkin, A. J.; Matochik, J. H.; Jons, P. A.; Cohen, R. M. *Journal of Neuroscience* 1998, 18(15), 5901-5907).

$5\text{-HT}_6$ ligands also show potential for the treatment of schizophrenia and depression. For example, clozapine (an effective clinical antipsychotic) has high affinity for the $5\text{-HT}_6$ receptor subtype. Also, several clinical antidepressants have high affinity for the receptor as well and act as antagonists at this site (Branchek, T. A.; Blackburn, T. P. *Annual Reviews in Pharmacology and Toxicology* 2000, 40, 319-334).

Impaired cognitive function is a core feature of schizophrenia, exhibiting numerous manifestations, including a fundamental defect in the patient's ability to manipulate available information. Weinberger et. al. International clinical psychopharmacology, 1997, 12, 38-40. The magnitude of the cognitive deficit in schizophrenia is considerable and remains relatively stable despite fluctuations in other symptoms. Id. The degree of dysfunction also has a high predictive value for long-term disability. Id. Good cognitive function depends upon the brain's ability to prioritize tasks and to switch from parallel processing to sequential processing when the processing load is excessive. Id. This requires working executive memory. Neuroimaging and functional analyses suggest that such cognitive function relies upon unimpaired prefrontal activity. Id. There is increasing evidence that antipsychotic drugs with 5-hydroxytryptamine-blocking activity (particularly $5\text{-HT}_{2a}$) produce better cognitive function in patients with schizophrenia than drugs with predominantly dopamine $(D)_2$-blocking activity (conventional neuroleptics). Id. Accordingly, improving or stabilizing cognitive function in patients suffering from schizophrenia through administration of antipsychotic drugs with 5-hydroxytryptamine-blocking activity will ideally lead to improved patient outcomes.

The neurocognitive deficits in schizophrenia are considered a separate area of the illness that is relatively independent of psychotic symptoms and closely related to functional outcome. These neurocognitive deficits include working memory, attention/vigilance, verbal learning and memory, visual learning and memory, reasoning and problem-solving, speed of processing, and social recognition (Green M F, Nuechterlein K H, Gold J M, et al. "Approaching a consensus cognitive battery for clinical trials in schizophrenia: the NIMH-MATRICS conference to select cognitive domains and test criteria", Biol. Psychiatry 2004; 56:301-307).

Further, recent in vivo studies in rats indicate $5\text{-HT}_6$ modulators may be useful in the treatment of movement disorders including epilepsy (Stean, T.; Routledge, C.; Upton, N. *British Journal of Pharmacology* 1999, 127 Proc. Supplement 131P and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M. *British Journal of Pharmacology* 2000, 130(7), 1606-1612).

Taken together, the above studies strongly suggest that compounds which are $5\text{-HT}_6$ receptor modulators, i.e. ligands, may be useful for therapeutic indications including: the treatment of symptoms associated with Alzheimer's disease, such as dementia, a deficit in memory, cognition, and learning; the treatment of personality disorders such as schizophrenia; the treatment of behavioral disorders, e.g., anxiety, depression and obsessive compulsive disorders; the treatment of ADD and ADHD; the treatment of motion or motor disorders such as Parkinson's disease and epilepsy; the treatment of diseases associated with neurodegeneration such as stroke and head trauma; or withdrawal from drug addiction including addiction to nicotine, alcohol, among others.

Because 5-$HT_6$ receptors are located almost exclusively in the brain, modulation of the receptors by parenterally administered drugs requires that the drugs cross the blood brain barrier. The blood brain barrier is composed of brain capillary endothelial cells with continuous tight junctions making it virtually impossible for compounds to enter into the brain around the cells. J. Bryan, Pharmaceutical Journal, 273 (2004) 475-476. Instead, access to the brain is limited to passive diffusion or active transport through the endothelial cells. G&G, Pharmaceutical Basis of Therapeutics, $10^{th}$ Ed at page 10. Accordingly, bioavailable parenterally administered compounds affecting 5-$HT_6$ activity must not only possess favorable solubility profiles in order to successfully enter the blood stream, but they also need to cross the blood brain barrier in order to target the 5-$HT_6$ receptors. Advantageously, this invention provides compounds which are capable of modulating 5-$HT_6$ receptor activity and are bioavailable.

Recent clinical and preclinical efforts on 5-$HT_6$ ligands have been reviewed by Rudy Schreiber, Andrew Sleight and Marie Woolley, "5-HT6 Receptors as Targets for the Treatment of Cognitive Deficits in Schizophrenia" in The Receptors Book The Serotonin Receptors, Humana Press, 2006, Pages 495-515, Edited by Bryan L. Roth; Johnson C N, Ahmed M, Miller N D, "5-HT6 receptor antagonists: prospects for the treatment of cognitive disorders including dementia" Curr. Opin. Drug Discov. Devel. 11 (5): 642-54 (September 2008), Jorg Holenz, Petrus J. Pauwels, Jose Luis Diaz, Ramon Merce, Xavier Codony, and Helmut Buschmann, "Medicinal chemistry strategies to 5-$HT_6$ receptor ligands as potential cognitive enhancers and antiobesity agents", Drug Discovery Today, 11 (7/8) April 2006, and Robin Emsley, "Drugs in development for the treatment of schizophrenia", Expert Opinion on Investigational Drugs, 18 (8) 1103-1118, August 2009.

Nine 5-$HT_6$ ligands have entered human clinical trials. Lu-AE-58054 from Lundbeck is in schizophrenia cognitive disorder Phase II trials, SAM-531 from Wyeth is in Alzheimer's disease Phase II trials, SYN-114 from Synosia Therapeutics is in Alzheimer's disease Phase I trials, PRX-07034 from EPIX Pharmaceuticals Inc, is in schizophrenia, Alzheimer's disease, and obesity Phase Ib trials, SUVN-502 from Suven Life Sciences Ltd. is in Alzheimer's disease Phase I trials, SB-742457 from GlaxoSmithKline is in cognitive dysfunction associated with Alzheimer's disease Phase II trials, LY-483518 from Lilly, which is licensed to Saegis Pharmaceuticals (SGS-518) is in cognitive impairment associated with schizophrenia Phase IIa trials, SAX-187 from Wyeth is currently in anxiety Phase I trials, and SB-271046 from GlaxoSmithKline was in Alzheimer's disease and schizophrenia Phase I trials but has been discontinued (probably because of low penetration of the blood-brain barrier).

The structures of 1-[(3-fluorophenyl)sulfonyl]-4-(1-piperazinyl)-1H-benzimidazole, 1-[(2-fluorophenyl)sulfonyl]-4-(1-piperazinyl)-1H-benzimidazole, 1-[(3-chlorophenyl)sulfonyl]-4-(1-piperazinyl)-1H-benzimidazole, 1-(1-naphthalenylsulfonyl)-4-(1-piperazinyl)-1H-benzimidazole, and 1-[(2,5-dichlorophenyl)sulfonyl]-4-(1-piperazinyl)-1H-benzimidazole were generated by ChemZoo, Inc. of Winston-Salem, N.C. in 2008 through the ChemSpider data base. However, the compounds do not appear to ever have been offered for sale. No information is provided as to their ability to bind to the 5-$HT_6$ receptor or to any pharmacological effect or use of these compounds. There is no evidence they were ever made and no method for making the compounds is provided.

The invention provides compounds useful as therapeutic agents in the treatment of a variety of conditions related to or affected by 5-$HT_6$ receptor activity, including psychoses (e.g., schizophrenia, anxiety, or depression), motor disorders (e.g., Parkinson's disease), anxiety, depression, drug addiction, obsessive compulsive disorder, attention deficit disorder, or any condition which is known to be related to or affected by the 5-$HT_6$ receptor. These and other features of this invention will become more apparent by the detailed description set forth herein below.

SUMMARY OF THE INVENTION

The present invention provides potent 5-$HT_6$ antagonist compounds of Formula I:

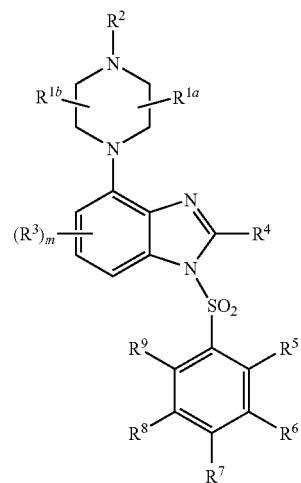

wherein the constituent variables are as defined below.

Another aspect of the invention provides a compound of Formula II:

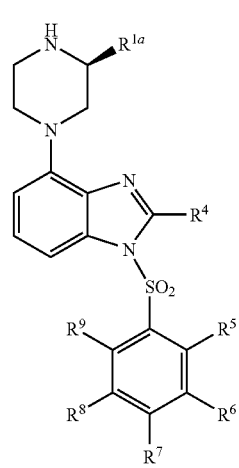

wherein the constituent variables are as defined below.

Another aspect of the invention provides a compound of Formula III:

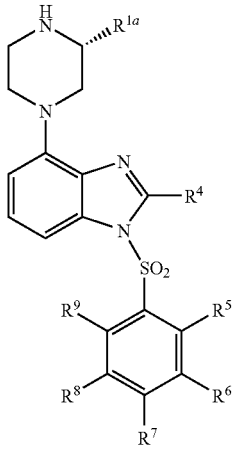

III wherein the constituent variables are as defined below.

Another aspect of the invention provides a compound of Formula IV:

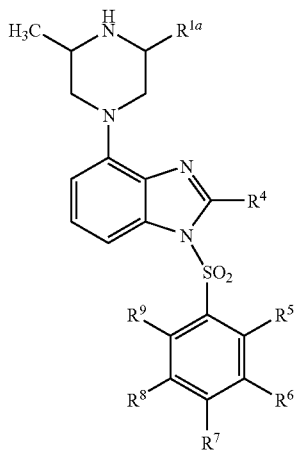

IV wherein the constituent variables are as defined below.

In other aspects, the invention provides compositions comprising a compound of the invention, and methods for making compounds of the invention. In further aspects, the invention provides methods for modulating 5-HT$_6$ in a subject, and methods for treating 5-HT$_6$-related disorders in a mammal in need thereof.

DETAILED DESCRIPTION OF THE INVENTION

In one aspect, the invention provides compounds of the Formula I:

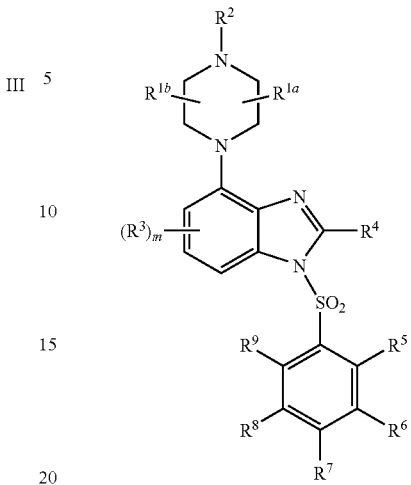

I wherein, $R^{1a}$ and $R^{1b}$ are each independently H or $C_1$-$C_6$alkyl, $C_2$-$C_6$alkenyl, or $C_2$-$C_6$alkynyl, each substituted with 0-4 substituents independently selected from the group consisting of $C_1$-$C_4$alkyl, $C_3$-$C_6$cycloalkyl, $C_3$-$C_6$cycloalkenyl, $C_2$-$C_6$alkenyl, $C_2$-$C_6$alkynyl, halo, nitro, cyano, hydroxy, —N($R^a$)$_2$, —C(O)$R^b$, —O$R^c$, and —S(O)$_p$$R^d$;

alternatively, $R^{1a}$ and $R^{1b}$ are taken together to form —(CH$_2$)$_n$—;

$R^2$ is H, $C_1$-$C_4$alkyl, —CHO or —C(O)($C_1$-$C_4$alkyl);

$R^3$ is independently at each occurrence halo, nitro, cyano, hydroxy, —N($R^a$)$_2$, $C_1$-$C_6$alkyl, $C_2$-$C_6$alkenyl, $C_2$-$C_6$alkynyl, $C_1$-$C_6$acyl, or $C_1$-$C_6$alkoxy, wherein each $C_1$-$C_6$alkyl, $C_2$-$C_6$alkenyl, $C_1$-$C_6$acyl or $C_1$-$C_6$alkoxy is substituted with 0-4 substituents independently selected from the group consisting of $C_1$-$C_4$alkyl, $C_3$-$C_6$cycloalkyl, $C_2$-$C_6$alkenyl, $C_2$-$C_6$alkynyl, halo, nitro, cyano, hydroxy, —N($R^a$)$_2$, —C(O)$R^b$, —O$R^c$ and —S(O)$_p$$R^d$;

$R^4$ is H, hydroxy, $C_1$-$C_6$alkyl, $C_2$-$C_6$alkenyl, $C_2$-$C_6$alkynyl, $C_1$-$C_6$acyl, $C_3$-$C_6$cycloalkyl, or $C_3$-$C_6$cycloalkenyl, wherein each $C_1$-$C_6$alkyl, $C_2$-$C_6$alkenyl, $C_2$-$C_6$alkynyl, $C_1$-$C_6$acyl, $C_3$-$C_6$cycloalkyl, or $C_3$-$C_6$cycloalkenyl is substituted with 0-4 substituents independently selected from the group consisting of $C_1$-$C_4$alkyl, $C_3$-$C_6$cycloalkyl, halo, nitro, cyano, hydroxy, —N($R^a$)$_2$, —C(O)$R^b$, —O$R^c$ and —S(O)$_p$$R^d$;

$R^5$, $R^6$, $R^7$, $R^8$, and $R^9$ are each independently H, halo, nitro, cyano, hydroxy, S(O)$_p$$R^d$, —N($R^a$)$_2$, $C_1$-$C_6$alkyl, $C_1$-$C_6$acyl, $C_1$-$C_6$alkoxy, $C_3$-$C_6$cycloalkyl, or $C_3$-$C_6$cycloalkenyl, wherein each $C_1$-$C_6$alkyl, $C_1$-$C_6$acyl, $C_1$-$C_6$alkoxy, $C_3$-$C_6$cycloalkyl, or $C_3$-$C_6$cycloalkenyl is substituted with 0-4 substituents independently selected from the group consisting of $C_1$-$C_4$alkyl, $C_3$-$C_6$cycloalkyl, $C_2$-$C_6$alkenyl, $C_2$-$C_6$alkynyl, halo, nitro, cyano, hydroxy, —N($R^a$)$_2$, —C(O)$R^b$, —O$R^c$ and —S(O)$_p$$R^d$;

alternatively, one of $R^5$ and $R^6$ or $R^6$ and $R^7$ are taken together with the carbon atoms to which they are attached to form a fused phenyl, $C_3$-$C_6$cycloalkyl, or $C_3$-$C_6$cycloalkenyl ring substituted with 0-3 $R^{10}$ groups;

$R^{10}$ is halo, nitro, cyano, hydroxy, S(O)$_p$$R^d$, —N($R^a$)$_2$, $C_1$-$C_6$alkyl, $C_1$-$C_6$acyl, $C_1$-$C_6$alkoxy, $C_3$-$C_6$cycloalkyl, or $C_3$-$C_6$cycloalkenyl, wherein each $C_1$-$C_6$alkyl, $C_1$-$C_6$acyl, $C_1$-$C_6$alkoxy, $C_3$-$C_6$cycloalkyl, or $C_3$-$C_6$cycloalkenyl is substituted with 0-4 substituents independently selected from the group consisting of $C_1$-$C_4$alkyl, $C_3$-$C_6$cycloalkyl, $C_3$-$C_6$cycloalkenyl, $C_2$-$C_6$alkenyl, $C_2$-$C_6$alkynyl, halo, nitro, cyano, hydroxy, phenyl, —N($R^a$)$_2$, —C(O)$R^b$, —O$R^c$, and —S(O)$_p R^d$;

each $R^a$ is independently H, —CHO, —C(O)($C_1$-$C_4$alkyl), —CO$_2$($C_1$-$C_4$alkyl), or $C_1$-$C_4$alkyl optionally substituted with halo;

each $R^b$ is independently H, —OH, $C_1$-$C_4$alkoxy-, —NH$_2$, —NH($C_1$-$C_4$alkyl), —N($C_1$-$C_4$alkyl)$_2$, or $C_1$-$C_4$alkyl optionally substituted with halo;

each $R^c$ is independently H, —C(O)($C_1$-$C_4$alkyl), or $C_1$-$C_4$alkyl optionally substituted with halo;

each $R^d$ is independently hydroxy or $C_1$-$C_4$alkyl optionally substituted with halo;

each p is independently 0, 1, or 2, m is 0, 1 or 2; and n is 1 or 2; or a tautomer, stereoisomer, or pharmaceutically acceptable salt thereof.

Another aspect of the invention provides a compound of Formula II:

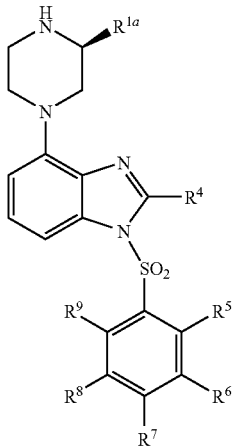

II wherein the variables are as described for the compound of Formula I.

Another aspect of the invention provides a compound of Formula III:

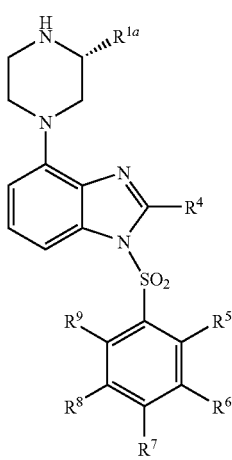

III wherein the variables are as described for the compound of Formula I.

Another aspect of the invention provides a compound of Formula IV:

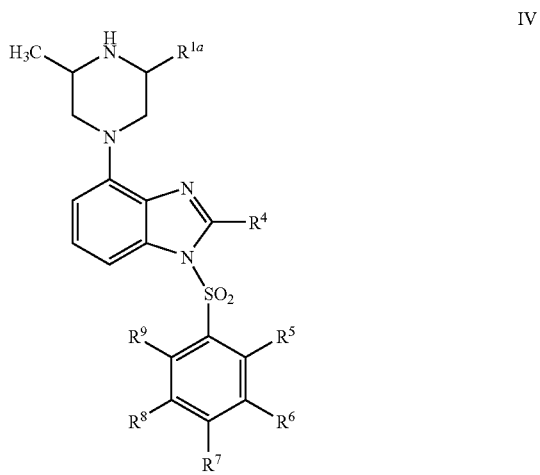

IV wherein the variables are as described for the compound of Formula I.

In one embodiment:

$R^{1a}$ and $R^{1b}$ are each independently H or $C_1$-$C_6$alkyl;

alternatively, $R^{1a}$ and $R^{1b}$ are taken together to form —(CH$_2$)$_n$—;

$R^2$ is H or $C_1$-$C_4$alkyl;

$R^3$ is independently at each occurrence hydroxyl or halo;

$R^4$ is H, hydroxy, or $C_1$-$C_6$alkyl;

$R^5$, $R^6$, $R^7$, $R^8$, and $R^9$ are each independently H, halo, hydroxy, $C_1$-$C_6$alkyl, or $C_1$-$C_6$alkoxy, wherein each $C_1$-$C_6$alkyl or $C_1$-$C_6$alkoxy is substituted with 0-3 halo;

alternatively, one of $R^5$ and $R^6$ or $R^6$ and $R^7$ are taken together with the carbon atoms to which they are attached to form a fused phenyl, $C_3$-$C_6$cycloalkyl, or $C_3$-$C_6$cycloalkenyl ring substituted with 0-3 $R^{19}$ groups;

each $R^{10}$ is independently halo, hydroxy, $C_1$-$C_6$alkyl, or $C_1$-$C_6$alkoxy, wherein each $C_1$-$C_6$alkyl or $C_1$-$C_6$alkoxy is substituted with 0-3 halo;

m is 0, 1 or 2; and n is 1 or 2.

In one embodiment, $R^2$ is H or $C_1$-$C_4$alkyl.

In one embodiment, $R^2$ is H.

In one embodiment, $R^4$ is $C_1$-$C_6$alkyl.

In one embodiment, $R^4$ is $C_1$-$C_4$alkyl.

In one embodiment, $R^4$ is methyl, ethyl, propyl, or butyl.

In one embodiment, $R^4$ is H.

In one embodiment, $R^3$ is halo.

In one embodiment, $R^{1a}$ and $R^{1b}$ are independently H or $C_1$-$C_4$alkyl.

In one embodiment, $R^{1a}$ and $R^{1b}$ are both H or —CH$_3$.

In one embodiment, $R^{1a}$ and $R^{1b}$ are both H.

In one embodiment, $R^{1a}$ is H and $R^{1b}$ is —CH$_3$.

In one embodiment, $R^2$ is H or $C_1$-$C_4$alkyl.

In one embodiment, $R^5$ is H or halo.

In one embodiment, $R^5$ is chloro.

In one embodiment, $R^5$ is $C_1$-$C_4$ alkoxy optionally substituted with halo.

In one embodiment, $R^5$ is $C_1$-$C_4$alkyl optionally substituted with halo.

In one embodiment, $R^6$ is H, halo, $C_1$-$C_4$alkyl optionally substituted with halo, or $C_1$-$C_4$alkoxy optionally substituted by halo.

In one embodiment, $R^6$ is —$OCF_3$.

In one embodiment, one of $R^5$, $R^6$, $R^7$, $R^8$, and $R^9$ is $C_1$-$C_4$alkyl optionally substituted by halo, one of $R^5$, $R^6$, $R^7$, $R^8$, and $R^9$ is halo, and the remaining three of $R^5$, $R^6$, $R^7$, $R^8$, and $R^9$ are H.

In one embodiment, $R^5$ is $C_1$-$C_4$alkyl optionally substituted by halo and $R^6$ is halo.

In one embodiment, $R^6$ is fluoro.

In one embodiment, $R^7$ is H or halo.

In one embodiment, $R^7$ is fluoro.

In one embodiment, $R^7$ is $C_1$-$C_4$alkoxy or $C_1$-$C_4$alkyl each optionally substituted with halo.

In one embodiment, one of $R^5$, $R^6$, $R^7$, $R^8$, and $R^9$ is halo and the remaining four of $R^5$, $R^6$, $R^7$, $R^8$, and $R^9$ are H.

In one embodiment, two of $R^5$, $R^6$, $R^7$, $R^8$, and $R^9$ are halo and the remaining three of $R^5$, $R^6$, $R^7$, $R^8$, and $R^9$ are H.

In one embodiment, one of $R^5$, $R^6$, $R^7$, $R^8$, and $R^9$ is alkyl optionally substituted by halo and the remaining four of $R^5$, $R^6$, $R^7$, $R^8$ and $R^9$ are H.

In one embodiment, $R^5$ and $R^6$ are taken together with the carbon atoms to which they are attached to form a fused phenyl, $C_3$-$C_6$cycloalkyl, or $C_3$-$C_6$cycloalkenyl ring each optionally substituted with $R^{10}$.

In one embodiment, $R^5$ and $R^6$ are taken together with the carbon atoms to which they are attached to form a fused phenyl ring.

In one embodiment, $R^5$ and $R^6$ are H.

In one embodiment, $R^{10}$ is halo.

In one embodiment, $R^6$ and $R^7$ are taken together with the carbon atoms to which they are attached to form a fused phenyl, $C_1$-$C_6$cycloalkyl, or $C_1$-$C_6$cycloalkenyl ring optionally substituted with halo.

In one embodiment, $R^6$ and $R^7$ are taken together with the carbon atoms to which they are attached to form a fused phenyl ring.

In one embodiment, $R^6$ is $OC_1$-$C_4$alkyl, $R^8$ is $C_1$-$C_4$alkyl, and $R^9$ is halo.

In another embodiment, $R^{1a}$ and $R^{1b}$ are H, $R^2$ is H or methyl, m is 0, $R^4$ is selected from the group consisting of H or $C_1$-$C_6$alkyl; and $R^5$, $R^6$, $R^7$, $R^8$, and $R^9$ are each H or halo.

In one embodiment thereof, $R^4$ is H.

In one embodiment, $R^6$ is F.

In one embodiment, $R^7$, $R^8$, and $R^9$ are each H.

In one embodiment, $R^4$ is methyl.

In one embodiment, the compounds of formula I exclude 1-[(3-fluorophenyl)sulfonyl]-4-(1-piperazinyl)-1H-benzimidazole, 1-[(2-fluorophenyl)sulfonyl]-4-(1-piperazinyl)-1H-benzimidazole, 1-[(3-chlorophenyl)sulfonyl]-4-(1-piperazinyl)-1H-benzimidazole, 1-(1-naphthalenylsulfonyl)-4-(1-piperazinyl)-1H-benzimidazole, and 1-[(2,5-dichlorophenyl)sulfonyl]-4-(1-piperazinyl)-1H-benzimidazole.

Illustrative compounds of formula I are:
4-(4-methylpiperazin-1-yl)-1-(naphthalen-1-ylsulfonyl)-1H-benzo[d]imidazole;
1-(naphthalen-1-ylsulfonyl)-4-(piperazin-1-yl)-1H-benzo[d]imidazole;
1-(phenylsulfonyl)-4-(piperazin-1-yl)-1H-benzo[d]imidazole;
2-methyl-1-(1-naphthylsulfonyl)-4-piperazin-1-yl-1H-benzimidazole;
2-methyl-1-(phenylsulfonyl)-4-piperazin-1-yl-1H-benzimidazole;
2-ethyl-1-(phenylsulfonyl)-4-piperazin-1-yl-1H-benzimidazole;
4-(4-ethylpiperazin-1-yl)-1-(phenylsulfonyl)-1H-benzimidazole;
2-butyl-1-(phenylsulfonyl)-4-piperazin-1-yl-1H-benzimidazole;
2-methyl-4-(4-methylpiperazin-1-yl)-1-(1-naphthylsulfonyl)-1H-benzimidazole;
1-[(4-chlorophenyl)sulfonyl]-4-piperazin-1-yl-1H-benzimidazole;
1-[(2-chlorophenyl)sulfonyl]-4-piperazin-1-yl-1H-benzimidazole;
4-(4-methylpiperazin-1-yl)-1-(phenylsulfonyl)-1H-benzimidazole;
1-[(4-methoxyphenyl)sulfonyl]-2-methyl-4-piperazin-1-yl-1H-benzimidazole;
2-methyl-4-piperazin-1-yl-1-{[3-(trifluoromethoxy)phenyl]sulfonyl}-1H-benzimidazole;
1-[(2-chlorophenyl)sulfonyl]-2-methyl-4-piperazin-1-yl-1H-benzimidazole;
1-[(3-chlorophenyl)sulfonyl]-2-methyl-4-piperazin-1-yl-1H-benzimidazole;
1-[(4-chlorophenyl)sulfonyl]-2-methyl-4-piperazin-1-yl-1H-benzimidazole;
2-methyl-1-[(3-methylphenyl)sulfonyl]-4-piperazin-1-yl-1H-benzimidazole;
1-[(3-chlorophenyl)sulfonyl]-4-piperazin-1-yl-1H-benzimidazole;
1-[(4-fluorophenyl)sulfonyl]-4-piperazin-1-yl-1H-benzimidazole;
1-[(2-fluorophenyl)sulfonyl]-4-piperazin-1-yl-1H-benzimidazole;
1-[(3-fluorophenyl)sulfonyl]-4-piperazin-1-yl-1H-benzimidazole;
1-(2-naphthylsulfonyl)-4-piperazin-1-yl-1H-benzimidazole;
1-[(4-methoxyphenyl)sulfonyl]-4-piperazin-1-yl-1H-benzimidazole;
4-piperazin-1-yl-1-{[4-(trifluoromethoxy)phenyl]sulfonyl}-1H-benzimidazole;
1-[(3-fluorophenyl)sulfonyl]-2-methyl-4-piperazin-1-yl-1H-benzimidazole;
1-[(4-methylphenyl)sulfonyl]-4-piperazin-1-yl-1H-benzimidazole;
4-piperazin-1-yl-1-{[3-(trifluoromethoxy)phenyl]sulfonyl}-1H-benzimidazole;
1-[(3-chloro-4-fluorophenyl)sulfonyl]-4-piperazin-1-yl-1H-benzimidazole;
2-methyl-4-piperazin-1-yl-1-{[4-(trifluoromethoxy)phenyl]sulfonyl}-1H-benzimidazole;
2-methyl-1-[(4-methylphenyl)sulfonyl]-4-piperazin-1-yl-1H-benzimidazole;
1-[(2-fluorophenyl)sulfonyl]-2-methyl-4-piperazin-1-yl-1H-benzimidazole;
4-piperazin-1-yl-1-{[2-(trifluoromethoxy)phenyl]sulfonyl}-1H-benzimidazole;
1-[(3-methoxyphenyl)sulfonyl]-4-piperazin-1-yl-1H-benzimidazole;
1-[(4-methyl-1-naphthyl)sulfonyl]-4-piperazin-1-yl-1H-benzimidazole;
1-[(3-methylphenyl)sulfonyl]-4-piperazin-1-yl-1H-benzimidazole;
1-[(3-chloro-2-methylphenyl)sulfonyl]-4-piperazin-1-yl-1H-benzimidazole;
1-[(4-fluorophenyl)sulfonyl]-2-methyl-4-piperazin-1-yl-1H-benzimidazole;
1-[(2-methylphenyl)sulfonyl]-4-piperazin-1-yl-1H-benzimidazole;
4-piperazin-1-yl-1-{[4-(trifluoromethyl)phenyl]sulfonyl}-1H-benzimidazole;

4-piperazin-1-yl-1-{[2-(trifluoromethyl)phenyl]sulfonyl}-1H-benzimidazole;
4-piperazin-1-yl-1-{[3-(trifluoromethyl)phenyl]sulfonyl}-1H-benzimidazole;
2-methyl-1-(2-naphthylsulfonyl)-4-piperazin-1-yl-1H-benzimidazole;
1-[(2-methoxyphenyl)sulfonyl]-4-piperazin-1-yl-1H-benzimidazole;
1-[(3-methoxyphenyl)sulfonyl]-2-methyl-4-piperazin-1-yl-1H-benzimidazole;
2-methyl-4-piperazin-1-yl-1-{[4-(trifluoromethoxy)phenyl]sulfonyl}-1H-benzimidazole;
2-methyl-1-[(2-methylphenyl)sulfonyl]-4-piperazin-1-yl-1H-benzimidazole;
2-methyl-4-piperazin-1-yl-1-{[2-(trifluoromethyl)phenyl]sulfonyl}-1H-benzimidazole;
2-methyl-4-piperazin-1-yl-1-{[3-(trifluoromethyl)phenyl]sulfonyl}-1H-benzimidazole;
1-[(5-chloro-1-naphthyl)sulfonyl]-4-piperazin-1-yl-1H-benzimidazole;
2-methyl-1-[(4-methyl-1-naphthyl)sulfonyl]-4-piperazin-1-yl-1H-benzimidazole;
1-[(2-methoxyphenyl)sulfonyl]-2-methyl-4-piperazin-1-yl-1H-benzimidazole;
1-[(2-chlorophenyl)sulfonyl]-4-(3-methylpiperazin-1-yl)-1H-benzimidazole;
1-[(3-chlorophenyl)sulfonyl]-4-(3-methylpiperazin-1-yl)-1H-benzimidazole;
1-[(3-methylphenyl)sulfonyl]-4-(3-methylpiperazin-1-yl)-1H-benzimidazole;
1-[(2-methoxyphenyl)sulfonyl]-4-(3-methylpiperazin-1-yl)-1H-benzimidazole;
4-(3-methylpiperazin-1-yl)-1-{[2-(trifluoromethoxy)phenyl]sulfonyl}-1H-benzimidazole;
1-[(3-chloro-2-methylphenyl)sulfonyl]-4-(3-methylpiperazin-1-yl)-1H-benzimidazole;
1-[(2-chlorophenyl)sulfonyl]-2-(1-methylethyl)-4-piperazin-1-yl-1H-benzimidazole;
1-[(3-chlorophenyl)sulfonyl]-2-(1-methylethyl)-4-piperazin-1-yl-1H-benzimidazole;
2-(1-methylethyl)-1-(naphthalen-1-ylsulfonyl)-4-piperazin-1-yl-1H-benzimidazole;
1-[(5-chloronaphthalen-1-yl)sulfonyl]-2-(1-methylethyl)-4-piperazin-1-yl-1H-benzimidazole;
2-(1-methylethyl)-4-piperazin-1-yl-1-{[2-(trifluoromethoxy)phenyl]sulfonyl}-1H-benzimidazole;
2-(1-methylethyl)-1-[(4-methylnaphthalen-1-yl)sulfonyl]-4-piperazin-1-yl-1H-benzimidazole;
1-[(5-chloro-2-methoxyphenyl)sulfonyl]-4-piperazin-1-yl-1H-benzimidazole;
1-[(5-bromo-2-methoxyphenyl)sulfonyl]-4-piperazin-1-yl-1H-benzimidazole;
1-[(2,5-dimethoxyphenyl)sulfonyl]-4-piperazin-1-yl-1H-benzimidazole;
1-[(2-methoxy-5-methylphenyl)sulfonyl]-4-piperazin-1-yl-1H-benzimidazole;
1-[(2-methoxy-4-methylphenyl)sulfonyl]-4-piperazin-1-yl-1H-benzimidazole;
1-[(2-chloro-6-methylphenyl)sulfonyl]-4-piperazin-1-yl-1H-benzimidazole;
1-{[(2-chloro-5-(trifluoromethyl)phenyl]sulfonyl}-4-piperazin-1-yl-1H-benzimidazole;
1-[(2-fluoro-5-methylphenyl)sulfonyl]-4-piperazin-1-yl-1H-benzimidazole;
1-[(2-fluoro-3-methylphenyl)sulfonyl]-4-piperazin-1-yl-1H-benzimidazole;
1-[(3-fluoro-2-methoxyphenyl)sulfonyl]-4-piperazin-1-yl-1H-benzimidazole;
1-[(2-chlorophenyl)sulfonyl]-4-[(3R)-3-methylpiperazin-1-yl]-1H-benzimidazole;
1-[(3-chlorophenyl)sulfonyl]-4-[(3R)-3-methylpiperazin-1-yl]-1H-benzimidazole;
1-[(3-chloro-2-methylphenyl)sulfonyl]-4-[(3R)-3-methylpiperazin-1-yl]-1H-benzimidazole;
4-[(3R)-3-methylpiperazin-1-yl]-1-(naphthalen-1-ylsulfonyl)-1H-benzimidazole;
1-[(2-chlorophenyl)sulfonyl]-4-[(3S)-3-methylpiperazin-1-yl]-1H-benzimidazole;
1-[(3-chlorophenyl)sulfonyl]-4-[(3S)-3-methylpiperazin-1-yl]-1H-benzimidazole;
4-[(3S)-3-methylpiperazin-1-yl]-1-(naphthalen-1-ylsulfonyl)-1H-benzimidazole;
1-[(3-chloro-2-methylphenyl)sulfonyl]-4-[(3S)-3-methylpiperazin-1-yl]-1H-benzimidazole;
1-[(2,3-difluorophenyl)sulfonyl]-4-piperazin-1-yl-1H-benzimidazole;
1-[(2,5-difluorophenyl)sulfonyl]-4-piperazin-1-yl-1H-benzimidazole;
1-[(2-chloro-5-fluorophenyl)sulfonyl]-4-piperazin-1-yl-1H-benzimidazole;
1-[(2,6-dichlorophenyl)sulfonyl]-4-piperazin-1-yl-1H-benzimidazole;
1-[(3-fluoro-2-methylphenyl)sulfonyl]-4-piperazin-1-yl-1H-benzimidazole;
1-[(3-chloro-5-fluorophenyl)sulfonyl]-4-piperazin-1-yl-1H-benzimidazole;
1-[(2-ethoxyphenyl)sulfonyl]-2-methyl-4-piperazin-1-yl-1H-benzimidazole;
1-[(5-chloro-2-methoxy-4-methylphenyl)sulfonyl]-4-piperazin-1-yl-1H-benzimidazole;
2-methyl-4-(3-methylpiperazin-1-yl)-1-(phenylsulfonyl)-1H-benzimidazole;
2-methyl-4-(3-methylpiperazin-1-yl)-1-(naphthalen-1-ylsulfonyl)-1H-benzimidazole;
1-[(2-chlorophenyl)sulfonyl]-2-methyl-4-(3-methylpiperazin-1-yl)-1H-benzimidazole;
1-[(3-fluorophenyl)sulfonyl]-2-methyl-4-(3-methylpiperazin-1-yl)-1H-benzimidazole;
1-[(3-chloro-2-methylphenyl)sulfonyl]-2-methyl-4-(3-methylpiperazin-1-yl)-1H-benzimidazole;
4-[(3R,5S)-3,5-dimethylpiperazin-1-yl]-2-methyl-1-(phenylsulfonyl)-1H-benzimidazole;
4-[(3R,5S)-3,5-dimethylpiperazin-1-yl]-2-methyl-1-(naphthalen-1-ylsulfonyl)-1H-benzimidazole;
1-[(2-chlorophenyl)sulfonyl]-4-[(3R,5S)-3,5-dimethylpiperazin-1-yl]-2-methyl-1H-benzimidazole;
4-[(3R,5S)-3,5-dimethylpiperazin-1-yl]-1-[(3-fluorophenyl)sulfonyl]-2-methyl-1H-benzimidazole;
1-[(3-chloro-2-methylphenyl)sulfonyl]-4-[(3R,5S)-3,5-dimethylpiperazin-1-yl]-2-methyl-1H-benzimidazole;
6-fluoro-1-(naphthalen-1-ylsulfonyl)-4-piperazin-1-yl-1H-benzimidazole;
1-[(2-chlorophenyl)sulfonyl]-6-fluoro-4-piperazin-1-yl-1H-benzimidazole;
6-fluoro-1-(phenylsulfonyl)-4-piperazin-1-yl-1H-benzimidazole;
4-[(1S,4S)-2,5-diazabicyclo[2.2.1]hept-2-yl]-1-(phenylsulfonyl)-1H-benzimidazole;
4-[(1S,4S)-2,5-diazabicyclo[2.2.1]hept-2-yl]-1-(naphthalen-1-ylsulfonyl)-1H-benzimidazole;
1-[(2-chlorophenyl)sulfonyl]-4-[(1S,4S)-2,5-diazabicyclo[2.2.1]hept-2-yl]-1H-benzimidazole;
4-[(1S,4S)-2,5-diazabicyclo[2.2.1]hept-2-yl]-1-[(3-fluorophenyl)sulfonyl]-1H-benzimidazole;
1-[(3-chloro-2-methylphenyl)sulfonyl]-4-[(1S,4S)-2,5-diazabicyclo[2.2.1]hept-2-yl]-1H-benzimidazole;
4-[(1S,4S)-2,5-diazabicyclo[2.2.1]hept-2-yl]-2-methyl-1-(phenylsulfonyl)-1H-benzimidazole;
4-[(1S,4S)-2,5-diazabicyclo[2.2.1]hept-2-yl]-2-methyl-1-(naphthalen-1-ylsulfonyl)-1H-benzimidazole;

1-[(2-chlorophenyl)sulfonyl]-4-[(1S,4S)-2,5-diazabicyclo [2.2.1]hept-2-yl]-2-methyl-1H-benzimidazole;
4-[(1S,4S)-2,5-diazabicyclo[2.2.1]hept-2-yl]-1-[(3-fluorophenyl)sulfonyl]-2-methyl-1H-benzimidazole;
1-[(3-chloro-2-methylphenyl)sulfonyl]-4-[(1S,4S)-2,5-diazabicyclo[2.2.1]hept-2-yl]-2-methyl-1H-benzimidazole;
2-methyl-4-[(3R)-3-methylpiperazin-1-yl]-1-(phenylsulfonyl)-1H-benzimidazole;
2-methyl-4-[(3R)-3-methylpiperazin-1-yl]-1-(1-naphthylsulfonyl)-1H-benzimidazole;
2-methyl-4-[(3S)-3-methylpiperazin-1-yl]-1-(phenylsulfonyl)-1H-benzimidazole;
2-methyl-4-[(3S)-3-methylpiperazin-1-yl]-1-(1-naphthylsulfonyl)-1H-benzimidazole;
4-(3-ethylpiperazin-1-yl)-1-(1-naphthylsulfonyl)-1H-benzimidazole;
4-(3-ethylpiperazin-1-yl)-1-(phenylsulfonyl)-1H-benzimidazole;
4-(3-isopropylpiperazin-1-yl)-1-(phenylsulfonyl)-1H-benzimidazole;
4-(3-isopropylpiperazin-1-yl)-1-(1-naphthylsulfonyl)-1H-benzimidazole;
1-[(2-chlorophenyl)sulfonyl]-4-(3-isopropylpiperazin-1-yl)-1H-benzimidazole;
4-(3-isobutylpiperazin-1-yl)-1-(phenylsulfonyl)-1H-benzimidazole;
4-(3-isobutylpiperazin-1-yl)-1-(1-naphthylsulfonyl)-1H-benzimidazole;
1-[(2-chlorophenyl)sulfonyl]-4-(3-isobutylpiperazin-1-yl)-1H-benzimidazole;
1-[(5-chloro-1-naphthyl)sulfonyl]-2-methyl-4-[(3S)-3-methylpiperazin-1-yl]-1H-benzimidazole;
1-[(5-chloro-1-naphthyl)sulfonyl]-2-methyl-4-[(3R)-3-methylpiperazin-1-yl]-1H-benzimidazole;
4-(3-methylpiperazin-1-yl)-1-(phenylsulfonyl)-1H-benzimidazole; and
4-(3-methylpiperazin-1-yl)-1-(1-naphthylsulfonyl)-1H-benzimidazole; or
a tautomer, stereoisomer, or pharmaceutically acceptable salt thereof.

In other aspects, the invention provides pharmaceutical compositions comprising compounds or pharmaceutically acceptable salts of the compounds of any of the present Formulas I-IV and a pharmaceutically acceptable carrier.

In other aspects, the invention provides that the pharmaceutically acceptable carrier suitable for oral administration and the composition comprises an oral dosage form.

In other aspects, the invention provides a method of treating a 5-HT$_6$-related disorder, comprising administering to a mammal in need thereof a compound of any of the Formulas I-IV in an amount effective to treat a 5-HT$_6$-related disorder.

In other aspects, the invention provides a method of treating a central nervous system (CNS) disease or disorder comprising administering to the subject a compound of Formulas I-IV; or
a tautomer, stereoisomer, or pharmaceutically acceptable salt thereof.

In other aspects, the central nervous system (CNS) disease or disorder is psychoses, anxiety, depression, epilepsy obsessive compulsive disorders, migraine, cognitive disorders, sleep disorders, feeding disorders, anorexia, bulimia, binge eating disorders, panic attacks, disorders resulting from withdrawal from drug abuse, cognitive impairment associated with schizophrenia, gastrointestinal disorders, irritable bowel syndrome, memory disorders, cognitive dysfunction associated with Alzheimer's disease, Parkinson's disease, Huntington's chorea, schizophrenia, attention deficit hyperactive disorder, neurodegenerative diseases characterized by impaired neuronal growth, and pain.

In another embodiment, the compound of any of the embodiments of the present invention exists as a pharmaceutically acceptable salt. More particularly, the pharmaceutically acceptable salt is hydrochloride (HCl).

Another embodiment of the invention provides a method of modulating 5-HT$_6$ receptor activity in a subject, comprising administering to the subject a compound of Formulas I-IV, wherein 5-HT$_6$ receptor activity is modulated in the subject.

In other aspects, the invention provides a method of synthesizing a compound of Formula I, comprising:

a) reacting a compound of Formula IA:

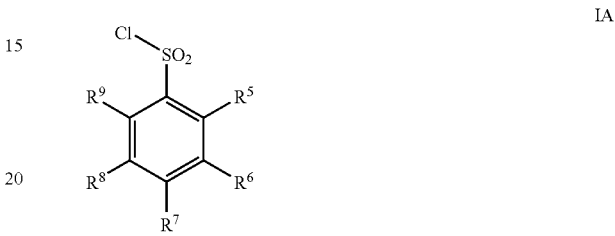

IA with a compound of Formula IB:

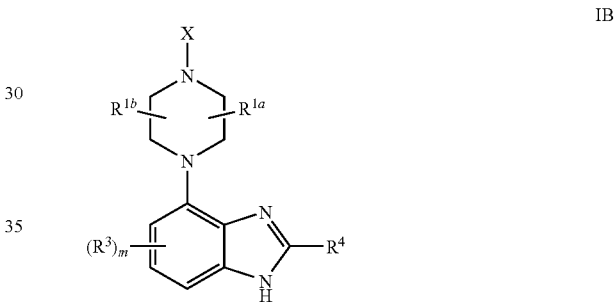

IB wherein,
X is $R^2$ or a protecting group;
to form a compound of Formula IC:

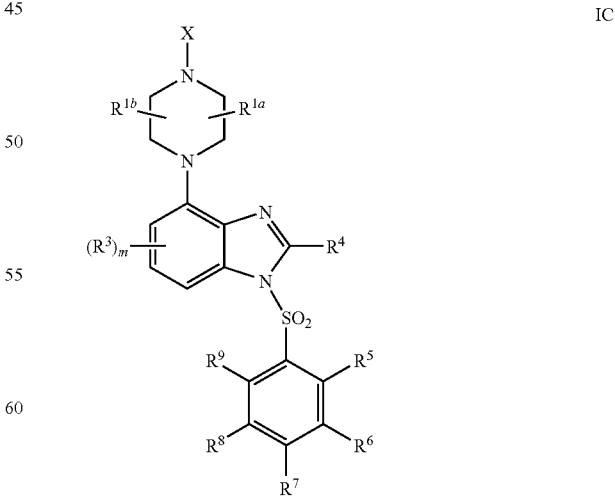

IC wherein $R^{1a}$, $R^{1b}$, and $R^2$-$R^9$ are defined as in Formula I; and
if X is $R^2$, then the compound of Formula I is formed; or if X is a protecting group, the process further comprises:
b) deprotecting the compound of Formula IC to form a deprotected compound;
wherein if $R^2$ is H, then compound of Formula I is formed; or if $R^2$ is other than H, the process further comprises:
c) reacting $G_A$-$R^2$ or $G_A$=$R^2$ with the deprotected compound;
wherein $G_A$ is an activating group;
wherein the compound of Formula I is formed.

In one embodiment, the process of reacting of compounds of Formula IA with IB is performed in an aprotic solvent in the presence of a base.

In one embodiment, the base is sodium hydride (NaH).

In one embodiment, the protecting group is tert-butoxycarbonyl (Boc), benzyl, acetyl, p-methoxybenzyl (PMB), or benzyloxycarbonyl (Cbz).

In one embodiment, the deprotecting step comprises contacting the compound of Formula IC with trifluoroacetic acid (TFA).

In one embodiment, $G_A$ is halo, tosylate, mesylate, triflate, or oxo.

In one embodiment, $G_A$ is oxo and the step of reacting $G_A$=$R^2$ with the deprotected compound comprises reductive amination in the presence of a boron-reducing agent.

In another aspect of the invention, the process further comprises preparing a compound of Formula IB by:
a) reacting a compound of Formula ID:

ID with a compound of Formula IE:

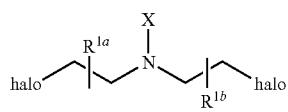

IE wherein,
halo is Cl, Br or I; and
wherein the compound of Formula IB is formed.

In one embodiment, X is a protecting group and the step of reacting the compound of Formula ID with the compound of Formula IE is performed in the presence of a base.

In one embodiment, the base is sodium bicarbonate (NaHCO$_3$) and the reacting step is performed at above about 100° C.

In another aspect of the invention, the process further comprises preparing a compound of Formula IB by reacting $R^4$—C(OEt)$_3$ with a compound of Formula IF:

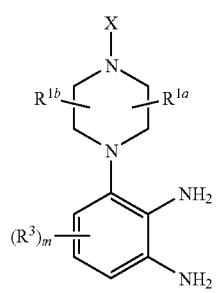

IF wherein the compound of Formula IB is formed.

In one embodiment, the step of reacting $R^4$—C(OEt)$_3$ with the compound of Formula IF is performed in the presence of montmorillonite KSF and toluene.

In another aspect of the invention, the process further comprises preparing a compound of Formula IF by hydrogenating a compound of Formula IG:

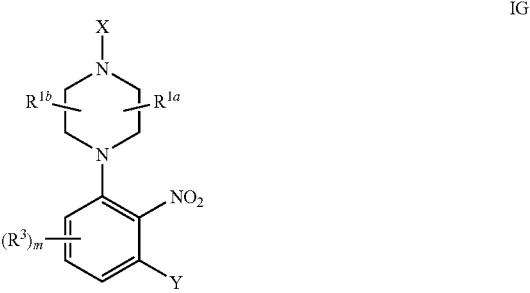

IG wherein,
Y is N$_3$ or NO$_2$.

In one embodiment, the hydrogenating step is performed in the presence of H$_2$ and palladium on carbon (H$_2$/Pd—C).

In another aspect of the invention, Y is NO$_2$ and the process further comprises preparing a compound of Formula IG by:
(a) reacting 2,3-dinitroaniline with sodium nitrate (NaNO$_2$) to form a (2,3-dinitrophenyl)diazonium compound; and
(b) contacting the dinitrophenyl)diazonium compound with a compound of Formula IH:

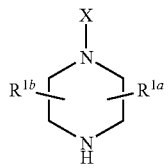

IH wherein the compound of Formula IG is formed.

In one embodiment, the step of reacting 2,3-dinitroaniline with sodium nitrate (NaNO$_2$) is performed in the presence of acetic acid (AcOH) and copper bromide (CuBr).

In one embodiment, the contacting step is performed in the presence of 2,2'-bis(diphenylphosphino)-1,1'-binaphthyl (BINAP), tris(dibenzylideneacetone)dipalladium (Pd$_2$(dba)$_3$), cesium carbonate (Cs$_2$CO$_3$), and toluene.

In one embodiment, the 2,3-dinitroaniline is prepared by reacting N-(3-nitrophenyl)acetamide with nitric acid (HNO$_3$) and sulfuric acid (H$_2$SO$_4$).

In another aspect of the invention, Y is N$_3$ and the process further comprises preparing a compound of Formula IG by:
(a) reacting sodium azide with 1,3-difluoro-2-nitrobenzene to form 1-azido-3-fluoro-2-nitrobenzene; and
(b) contacting 1-azido-3-fluoro-2-nitrobenzene with a compound of Formula IH:

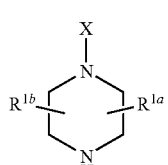

IH wherein the compound of Formula IG is formed.

In one embodiment, the contacting step is performed in the presence of N,N-diisopropylethylamine (DIPEA).

In one embodiment, any of the foregoing process steps are performed in a protic solvent, an aprotic solvent, a polar solvent, a nonpolar solvent, a protic polar solvent, an aprotic nonpolar solvent, or an aprotic polar solvent.

In one embodiment, any of the foregoing process steps comprises a purification step comprising at least one of: filtration, extraction, chromatography, trituration, or recrystallization.

In another embodiment, any of the foregoing process steps comprises an analytical step comprising liquid chromatography (LC), mass spectroscopy (MS), liquid chromatography/mass spectroscopy (LC/MS), gas chromatography (GC), gas chromatography/mass spectroscopy (GC/MS), nuclear magnetic resonance (NMR), thin layer chromatography (TLC), melting point (MP) analysis, optical rotation (OR) or elemental analysis.

Representative "pharmaceutically acceptable salts" include but are not limited to, e.g., water-soluble and water-insoluble salts, such as the acetate, aluminum, amsonate (4,4-diaminostilbene-2,2-disulfonate), benzathine (N,N'-dibenzylethylenediamine), benzenesulfonate, benzoate, bicarbonate, bismuth, bisulfate, bitartrate, borate, bromide, butyrate, calcium, calcium edetate, camsylate (camphorsulfonate), carbonate, chloride, choline, citrate, clavulariate, diethanolamine, dihydrochloride, diphosphate, edetate, edisylate (camphorsulfonate), esylate (ethanesulfonate), ethylenediamine, fumarate, gluceptate (glucoheptonate), gluconate, glucuronate, glutamate, hexafluorophosphate, hexylresorcinate, hydrabamine (N,N'-bis(dehydroabietyl) ethylenediamine), hydrobromide, hydrochloride, hydroxynaphthoate, 1-hydroxy-2-naphthoate, 3-hydroxy-2-naphthoate, iodide, isothionate (2-hydroxyethanesulfonate), lactate, lactobionate, laurate, lauryl sulfate, lithium, magnesium, malate, maleate, mandelate, meglumine (1-deoxy-1-(methylamino)-D-glucitol), mesylate, methyl bromide, methylnitrate, methylsulfate, mucate, napsylate, nitrate, N-methylglucamine ammonium salt, oleate, oxalate, palmitate, pamoate (4,4'-methylenebis-3-hydroxy-2-naphthoate, or embonate), pantothenate, phosphate, picrate, polygalacturonate, potassium, propionate, p-toluenesulfonate, salicylate, sodium, stearate, subacetate, succinate, sulfate, sulfosalicylate, suramate, tannate, tartrate, teoclate (8-chloro-3,7-dihydro-1,3-dimethyl-1H-purine-2,6-dione), triethiodide, tromethamine (2-amino-2-(hydroxymethyl)-1,3-propanediol), valerate, and zinc salts.

Some compounds within the present invention possess one or more chiral centers, and the present invention includes each separate enantiomer of such compounds as well as mixtures of the enantiomers. Where multiple chiral centers exist in compounds of the present invention, the invention includes each combination as well as mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

An "effective amount" when used in connection a compound of the present invention of this invention is an amount effective for inhibiting mTOR or PI3K in a subject.

DEFINITIONS

The following definitions are used in connection with the compounds of the present invention unless the context indicates otherwise. In general, the number of carbon atoms present in a given group is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are arrived at by naming from left to right the terminal portion of the functionality followed by the adjacent functionality toward the point of attachment. For example, the substituent "arylalkyloxycabonyl" refers to the group ($C_6$-$C_{14}$aryl)-($C_1$-$C_6$alkyl)-O—C(O)—. It is understood that the above definitions are not intended to include impermissible substitution patterns (e.g., methyl substituted with 5 fluoro groups, two hydroxyl groups on a single carbon atom, a hydroxyl group on a non-aromatic double bond). Such impermissible substitution patterns are well known to the skilled artisan. In each of the below groups, when a subgroup is designated with a multiple occurrence, each occurrence is selected independently. For example, in di($C_1$-$C_6$alkyl) amino—e.g. ($C_1$-$C_6$alkyl)$_2$N—, the $C_1$-$C_6$alkyl groups can be the same or different.

"Activating" a compound refers to reacting the compound at a center with a reagent to introduce at the center an activating group, wherein the activating group is optionally converted to another activating group in one or more steps. Examples of activating include halogenation at a carbon center, optionally followed by hydroboration wherein the halogen group is converted to an optionally substituted borane; tosylation, mesylation, or triflation at an oxygen center; and nitration at a carbon center optionally followed by reduction of the nitro group to an amino group and conversion of the amino group to a diazo group.

"Activating group" is a group that, when bound to a center, increases the reactivity at that center. Non-limiting examples of an activating group include a substituent bound to an electrophilic center and capable of being displaced by a nucleophile; a substituent bound to a nucleophilic center and capable of being displaced by an electrophile; a substituent capable of being displaced by a radical; or a substituent bound to a center wherein, following gain or loss of an electron, the substituent is capable of leaving as an anion or cation with formation of a radical at the center.

"Acyl-" refers to a group having a straight, branched, or cyclic configuration or a combination thereof, attached to the parent structure through a carbonyl functionality. Such groups may be saturated or unsaturated, aliphatic or aromatic, and carbocyclic or heterocyclic. The carbon count includes the carbonyl carbon atom. Examples of a $C_1$-$C_8$acyl-group include HC(O)—, acetyl-, benzoyl-, p-toluoyl, nicotinoyl-, propionyl-, isobutyryl-, oxalyl-, and the like. Lower-acyl- refers to acyl groups containing one to four carbons. An acyl-group can be unsubstituted or substituted with one or more of the following groups: halogen, H$_2$N—, ($C_1$-$C_6$alkyl) amino-, di($C_1$-$C_6$alkyl)amino-, ($C_1$-$C_6$alkyl)C(O)N($C_1$-$C_3$alkyl)-, ($C_1$-$C_6$alkyl)carbonylamido-, HC(O)NH—, H$_2$NC(O)—, ($C_1$-$C_6$alkyl)NHC(O)—, di($C_1$-$C_6$alkyl)NC(O)—, —CN, hydroxyl, $C_1$-$C_6$alkoxy-, $C_1$-$C_6$alkyl-, HO$_2$C—, ($C_1$-$C_6$alkoxy)carbonyl-, $C_1$-$C_8$acyl-, $C_6$-$C_{14}$aryl-, $C_1$-$C_9$heteroaryl-, or $C_3$-$C_8$cycloalkyl-.

"Alkenyl-" refer to a straight or branched chain unsaturated hydrocarbon containing at least one double bond. Where E- and/or Z-isomers are possible, the term "alkenyl" is intended to include all such isomers. Examples of a $C_2$-$C_6$alkenyl- group include, but are not limited to, ethylene, propylene, 1-butylene, 2-butylene, isobutylene, sec-butylene, 1-pentene, 2-pentene, isopentene, penta-1,4-dien-1-yl, 1-hexene, 2-hexene, 3-hexene, and isohexene. An alkenyl-group can be unsubstituted or substituted with one or more of the following groups: halogen, $H_2N—$, $(C_1-C_6alkyl)amino-$, $di(C_1-C_6alkyl)amino-$, $(C_1-C_6alkyl)C(O)N(C_1-C_3alkyl)-$, $(C_1-C_6alkyl)carbonylamido-$, $HC(O)NH—$, $H_2NC(O)—$, $(C_1-C_6alkyl)NHC(O)—$, $di(C_1-C_6alkyl)NC(O)—$, $—CN$, hydroxyl, $C_1-C_6alkoxy-$, $C_1-C_6alkyl-$, $HO_2C—$, $(C_1-C_6alkoxy)carbonyl-$, $C_1-C_8acyl-$, $C_6-C_{14}aryl-$, $C_1-C_9heteroaryl-$, and $C_3-C_8cycloalkyl-$.

"Alkoxy-" refers to the group R—O— where R is an alkyl group, as defined below. Exemplary $C_1-C_6alkoxy-$groups include but are not limited to methoxy, ethoxy, n-propoxy, 1-propoxy, n-butoxy and t-butoxy. An alkoxy group can be unsubstituted or substituted with one or more of the following groups: halogen, hydroxyl, $C_1-C_6alkoxy-$, $H_2N—$, $(C_1-C_6alkyl)amino-$, $di(C_1-C_6alkyl)amino-$, $(C_1-C_6alkyl)C(O)N(C_1-C_3alkyl)-$, $(C_1-C_6alkyl)carbonylamido-$, $HC(O)NH—$, $H_2NC(O)—$, $(C_1-C_6alkyl)NHC(O)—$, $di(C_1-C_6alkyl)NC(O)—$, $—CN$, $C_1-C_6alkoxy-$, $HO_2C—$, $(C_1-C_6alkoxy)carbonyl-$, $C_1-C_8acyl-$, $C_6-C_{14}aryl-$, $C_1-C_9heteroaryl-$, $C_3-C_8cycloalkyl-$, $C_1-C_6haloalkyl-$, $C_1-C_6-aminoalkyl-$, $(C_1-C_6alkyl)carboxy-$, $C_1-C_6-carbonylamidoalkyl-$, or $O_2N—$.

"Alkyl-" refers to a hydrocarbon chain that may be a straight chain or branched chain, containing the indicated number of carbon atoms, for example, a $C_1-C_{10}alkyl$-group may have from 1 to 10 (inclusive) carbon atoms in it. In the absence of any numerical designation, "alkyl" is a chain (straight or branched) having 1 to 6 (inclusive) carbon atoms in it. Examples of $C_1-C_6alkyl$-groups include, but are not limited to, methyl, ethyl, propyl, butyl, pentyl, hexyl, isopropyl, isobutyl, sec-butyl, tert-butyl, isopentyl, neopentyl, and isohexyl. An alkyl-group can be unsubstituted or substituted with one or more of the following groups: halogen, $H_2N—$, $(C_1-C_6alkyl)amino-$, $di(C_1-C_6alkyl)amino-$, $(C_1-C_6alkyl)C(O)N(C_1-C_3alkyl)-$, $(C_1-C_6alkyl)carbonylamido-$, $HC(O)NH—$, $H_2NC(O)—$, $(C_1-C_6alkyl)NHC(O)—$, $di(C_1-C_6alkyl)NC(O)—$, $—CN$, hydroxyl, $C_1-C_6alkoxy-$, $HO_2C—$, $(C_1-C_6alkoxy)carbonyl-$, $C_1-C_8acyl-$, $C_6-C_{14}aryl-$, $C_1-C_9heteroaryl-$, $C_3-C_8cycloalkyl-$, $C_1-C_8haloalkyl-$, $C_1-C_6aminoalkyl-$, $(C_1-C_6alkyl)carboxy-$, $C_1-C_6-carbonylamidoalkyl-$, or $O_2N—$.

"Alkynyl-" refers to a straight or branched chain unsaturated hydrocarbon containing at least one triple bond. Examples of a $C_2-C_6alkynyl$-group include, but are not limited to, acetylene, propyne, 1-butyne, 2-butyne, isobutyne, sec-butyne, 1-pentyne, 2-pentyne, isopentyne, penta-1,4-diyn-1-yl, 1-hexyne, 2-hexyne, 3-hexyne, and isohexyne. An alkynyl group can be unsubstituted or substituted with one or more of the following groups: halogen, $H_2N—$, $(C_1-C_6alkyl)amino-$, $di(C_1-C_6alkyl)amino-$, $(C_1-C_6alkyl)C(O)N(C_1-C_3alkyl)-$, $(C_1-C_6alkyl)carbonylamido-$, $HC(O)NH—$, $H_2NC(O)—$, $(C_1-C_6alkyl)NHC(O)—$, $di(C_1-C_6alkyl)NC(O)—$, $—CN$, hydroxyl, $C_1-C_6alkoxy-$, $HO_2C—$, $(C_1-C_6alkoxy)carbonyl-$, $C_1-C_8acyl-$, $C_6-C_{14}aryl-$, $C_1-C_9heteroaryl-$, and $C_3-C_8cycloalkyl-$.

"Amino" refers to the group $H_2N—$.

Aryl- refers to an aromatic hydrocarbon group. Examples of an $C_6-C_{14}aryl$-group include, but are not limited to, phenyl, 1-naphthyl, 2-naphthyl, 3-biphen-1-yl, anthryl, tetrahydronaphthyl, fluorenyl, indanyl, biphenylenyl, and acenaphthenyl. An aryl group can be monocyclic or polycyclic as long as at least one ring is aromatic and the point of attachment is at an aromatic carbon atom. An aryl group can be unsubstituted or substituted with one or more of the following groups: $C_1-C_6alkyl-$, halogen, haloalkyl-, hydroxyl, hydroxyl($C_1-C_6alkyl$)-, $H_2N—$, aminoalkyl-, $di(C_1-C_6alkyl)amino-$, $HO_2C—$, $(C_1-C_6alkoxy)carbonyl-$, $(C_1-C_6alkyl)carboxy-$, $di(C_1-C_8alkyl)amido-$, $H_2NC(O)—$, $(C_1-C_6alkyl)amido-$, or $O_2N—$.

"(Aryl)alkyl-" refers to an alkyl group, as defined above, wherein one or more of the alkyl group's hydrogen atoms have been replaced with an aryl group as defined above. $(C_6-C_{14}Aryl)alkyl-$moieties include benzyl, benzhydryl, 1-phenylethyl, 2-phenylethyl, 3-phenylpropyl, 2-phenylpropyl, 1-naphthylmethyl, 2-naphthylmethyl and the like. An (aryl)alkyl-group can be unsubstituted or substituted with one or more of the following groups: halogen, $H_2N—$, hydroxyl, $(C_1-C_6alkyl)amino-$, $di(C_1-C_8alkyl)amino-$, $(C_1-C_6alkyl)C(O)N(C_1-C_3alkyl)-$, $(C_1-C_6alkyl)carbonylamido-$, $HC(O)NH—$, $H_2NC(O)—$, $(C_1-C_6alkyl)NHC(O)—$, $di(C_1-C_6alkyl)NC(O)—$, $—CN$, hydroxyl, $C_1-C_6alkoxy-$, $C_1-C_6alkyl-$, $HO_2C—$, $(C_1-C_6alkoxy)carbonyl-$, $C_1-C_8acyl-$, $C_6-C_{14}aryl-$, $C_1-C_8heteroaryl-$, $C_3-C_8cycloalkyl-$, $C_1-C_6haloalkyl-$, $C_1-C_6-aminoalkyl-$, $(C_1-C_6alkyl)carboxy-$, $C_1-C_6-carbonylamidoalkyl-$, or $O_2N—$.

A "CNS disease" or "CNS disorder" is a disease or disorder affecting or originating in the central nervous system, preferably a disease related to $5-HT_6$ activity or affected by $5-HT_6$ modulation. Particular CNS diseases or disorder include psychoses, anxiety, depression, epilepsy, migraine, cognitive disorders, sleep disorders, feeding disorders, anorexia, bulimia, binge eating disorders, panic attacks, disorders resulting from withdrawal from drug abuse, cognitive impairment associated with schizophrenia, gastrointestinal disorders, irritable bowel syndrome, memory disorders, obsessive compulsive disorders, cognitive dysfunction associated with Alzheimer's disease, ADD, ADHD, Restless Legs Syndrome (RLS), Parkinson's disease, Huntington's chorea, schizophrenia, attention deficit hyperactive disorder, neurodegenerative diseases characterized by impaired neuronal growth, and pain. A "CNS disease" or "CNS disorder" as used herein also includes the symptom of another disease, such as a cognitive disorders associated with schizophrenia.

"Cycloalkyl-" refers to a monocyclic saturated hydrocarbon ring. Representative examples of a $C_3-C_8cycloalkyl-$ include, but are not limited to, cyclopropyl, cyclobutyl, cyclopentyl, cyclohexyl, cycloheptyl, and cyclooctyl. A cycloalkyl- can be unsubstituted or independently substituted with one or more of the following groups: halogen, $H_2N—$, $(C_1-C_6alkyl)amino-$, $di(C_1-C_6alkyl)amino-$, $(C_1-C_6alkyl)C(O)N(C_1-C_3alkyl)-$, $(C_1-C_6alkyl)carbonylamido-$, $HC(O)NH—$, $H_2NC(O)—$, $(C_1-C_6alkyl)NHC(O)—$, $di(C_1-C_6alkyl)NC(O)—$, $—CN$, hydroxyl, $C_1-C_6alkoxy-$, $C_1-C_6alkyl-$, $HO_2C—$, $(C_1-C_6alkoxy)carbonyl-$, $C_1-C_8acyl-$, $C_6-C_{14}aryl-$, $C_1-C_8heteroaryl-$, or $C_3-C_8cycloalkyl-$, $C_1-C_6haloalkyl-$, $C_1-C_6-aminoalkyl-$, $(C_1-C_6alkyl)carboxy-$, $C_1-C_6-carbonylamidoalkyl-$, or $O_2N—$. Additionally, each of any two hydrogen atoms on the same carbon atom of the carbocyclic ring can be replaced by an oxygen atom to form an oxo (=O) substituent or the two hydrogen atoms can be replaced by an alkylenedioxy group so that the alkylenedioxy group, when taken together with the carbon atom to which it is attached, form a 5- to 7-membered heterocycle-containing two oxygen atoms.

"Deprotecting" refers to removal of a protecting group, such as removal of a benzyl or BOC group bound to an amine. Deprotecting may be preformed by heating and/or addition of reagents capable of removing protecting groups. In preferred embodiments, the deprotecting step involves addition of an acid, base, reducing agent, oxidizing agent, heat, or any combination thereof. One preferred method of removing BOC groups from amino groups is to add HCl or TFA to a solution. Many deprotecting reactions are well known in the art and are described in Protective Groups in Organic Synthesis, Greene and Wuts, John Wiley & Sons, New York, N.Y., (3$^{rd}$ Edition, 1999), the entire disclosure of which is herein incorporated by reference.

"Protecting group" or "$G_p$" with respect to amine groups, hydroxyl groups and sulfhydryl groups refers to forms of these functionalities which are protected from undesirable reaction with a protecting group known to those skilled in the art, such as those set forth in Protective Groups in Organic Synthesis, Greene, T. W.; Wuts, P. G. M., John Wiley & Sons, New York, N.Y., (3rd Edition, 1999), the entire disclosure of which is herein incorporated by reference, which protecting groups can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; carbamates; e.g. Boc; imides, such as phthalimide, Fmoc, Cbz, PMB, benzyl, and dithiosuccinimide; and others. Examples of protected or capped sulfhydryl groups include, but are not limited to, thioethers such as S-benzyl thioether, and S-4-picolyl thioether; substituted S-methyl derivatives such as hemithio, dithio and aminothio acetals; and others.

"Halo" or "halogen" refers to fluorine, chlorine, bromine, or iodine.

"Haloalkyl-" refers to an alkyl group, as defined above, wherein one or more of the hydrogen atoms has been replaced with —F, —Cl, —Br, or —I. Each substitution can be independently selected. Representative examples of an $C_1$-$C_6$haloalkyl-group include, but are not limited to, —CH$_2$F, —CCl$_3$, —CF$_3$, CH$_2$CF$_3$, —CH$_2$Cl, —CH$_2$CH$_2$Br, —CH$_2$CH$_2$I, —CH$_2$CH$_2$CH$_2$F, —CH$_2$CH$_2$CH$_2$Cl, —CH$_2$CH$_2$CH$_2$CH$_2$Br, —CH$_2$CH$_2$ CH$_2$CH$_2$I, —CH$_2$CH$_2$CH$_2$CH$_2$CH$_2$Br, —CH$_2$CH$_2$CH$_2$CH$_2$CH$_2$I, —CH$_2$CH(Br)CH$_3$, —CH$_2$CH(Cl)CH$_2$CH$_3$, —CH(F) CH$_2$CH$_3$ and —C(CH$_3$)$_2$(CH$_2$Cl).

"Heteroatom" refers to a sulfur, nitrogen, or oxygen atom.

"Hydroxy" or "hydroxyl" refers to the group HO—.

"Modulating 5-HT$_6$ receptor activity" refers to affecting (i.e. inhibition or stimulation) processes or signaling events associated with the 5-HT$_6$ receptor. Specifically, inhibition of 5-HT$_6$ increases levels of acetylcholine and glutamate in the brain, whereas 5-HT$_6$ receptor agonism or stimulation results in increased cellular cAMP.

"Nitro" refers to the group O$_2$N—.

"Oxo" refers to the atom (═O). As an activating group, 'oxo' groups are amenable to reductive amination by nucleophilic amine groups to form alkylamino or aminoalkyl substituents. Preferably, the reductive amination step takes place in the presence of a boron-containing reducing agent.

"Stereoisomer" or "stereoisomers" refer to compounds that differ in the chirality or atomic connectivity at one or more stereocenters. Stereoisomers include enantiomers, diastereomers, as well as cis-trans (E/Z) isomerism.

A "subject" or "patient" is a mammal, e.g., a human, mouse, rat, guinea pig, dog, cat, horse, cow, pig, or non-human primate, such as a monkey, chimpanzee, baboon or gorilla.

"Tautomer" refers to alternate forms of a compound that differ in the position of a proton, such as enol-keto or imine-enamine tautomers.

"Treating" or "treatment" of a disease in a subject refers to: inhibiting the disease or arresting its development; ameliorating a symptom of the disease; or causing regression of the disease. Accordingly, "treatment of Alzheimer's disease" as used herein encompasses amelioration of symptoms associated with Alzheimer's disease, such as the amelioration of Alzheimer's-related dementia or treatment of the cognitive dysfunction associated with Alzheimer's disease. Additionally, "treatment of schizophrenia" includes improving or stabilizing cognitive function and ameliorating cognitive impairment associated with schizophrenia.

The term "optionally substituted", unless otherwise specified, as used herein means that at least one hydrogen atom of the optionally substituted group has been substituted with halogen, H$_2$N—, ($C_1$-$C_6$alkyl)amino-, di($C_1$-$C_6$alkyl) amino-, ($C_1$-$C_6$alkyl)C(O)N($C_1$-$C_3$alkyl)-, ($C_1$-$C_6$alkyl)carbonylamido-, HC(O)NH—, H$_2$NC(O)—, ($C_1$-$C_6$alkyl)NHC (O)—, di($C_1$-$C_6$alkyl)NC(O)—, —CN, hydroxyl, $C_1$-$C_6$alkoxy-, $C_1$-$C_6$alkyl-, HO$_2$C—, ($C_1$-$C_6$alkoxy)carbonyl-, $C_1$-$C_8$acyl-, $C_6$-$C_{14}$aryl-, $C_1$-$C_9$heteroaryl-, or $C_3$-$C_8$cycloalkyl-. It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group etc.) are not intended for inclusion herein. In such cases, the maximum number of such substitutions is three. For example, serial substitutions of substituted aryl groups with two other substituted aryl groups are limited to substituted aryl-(substituted aryl)-substituted aryl.

The compounds of the present invention exhibit a 5-HT$_6$ modulating activity and, therefore, can be utilized in order to treat a patient suffering from a central nervous system (CNS) disease or disorder comprising administering to the subject a compound described herein, particularly a compound of Formulas I-IV.

In another embodiment, the (CNS) disease or disorder is psychoses, anxiety, depression, epilepsy obsessive compulsive disorders, migraine, cognitive disorders, sleep disorders, feeding disorders, anorexia, bulimia, binge eating disorders, panic attacks, disorders resulting from withdrawal from drug abuse, schizophrenia, gastrointestinal disorders, irritable bowel syndrome, memory disorders, cognitive dysfunction associated with Alzheimer's disease, Parkinson's disease, Huntington's chorea, schizophrenia, attention deficit hyperactive disorder, neurodegenerative diseases characterized by impaired neuronal growth, or pain.

Another embodiment of the invention provides a method for improving or stabilizing cognitive function in a subject comprising administering to the subject a compound described herein, particularly a compound of Formulas I-IV or a tautomer, stereoisomer, or pharmaceutically acceptable salt thereof.

In another embodiment, the cognitive function is stabilized or improved in a subject is suffering from schizophrenia.

For therapeutic use, the pharmacologically active compounds of any of the Formulas I-IV will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions of this invention include suitable dosage forms for oral, parenteral (including subcutaneous, intramuscular, intradermal and intravenous) bronchial or nasal administration. Thus, if a solid carrier is used, the preparation may be made into tablets, placed in a hard gelatin capsule in powder or pellet form, or in the form of a troche or lozenge. The solid carrier may contain conventional excipients such as binding agents, fillers, lubricants used to make tablets, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of any of the Formulas I-IV directly in parenteral formulations. The pharmaceutical compositions are prepared by conventional techniques appropriate to the desired preparation containing appropriate amounts of the active ingredient, that is, the compound of any of the Formulas I-IV according to the invention. See, for example, *Remington: The Science and Practice of Pharmacy*, 20th Edition. Baltimore, Md.: Lippincott Williams & Wilkins, 2000.

The dosage of the compounds of any of the Formulas I-IV to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that one skilled in the art would adjust the unit dosage form accordingly to reflect the relative level of activity. The decision as to the particular dosage to be employed (and the number of times to be administered per day is within the discretion of the physician, and may be varied by titration of the dosage to the particular circumstances of this invention to produce the desired therapeutic effect.

A suitable dose of a compound of any of the Formulas I-IV or pharmaceutical composition thereof for a mammal, including man, suffering from, or likely to suffer from any condition as described herein is an amount of active ingredient from about 0.01 .mg/kg to 10 mg/kg body weight. For parenteral administration, the dose may be in the range of 0.1 .mg/kg to 1 mg/kg body weight for intravenous administration. For oral administration, the dose may be in the range about 0.1 .mg/kg to 5 mg/kg body weight. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The amount of the compound of the present invention or a pharmaceutically acceptable salts thereof is an amount that is effective for modulating 5-$HT_6$ activity in a subject. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The effective dosage amounts described herein refer to total amounts administered; that is, if more than one compound of the present invention or a pharmaceutically acceptable salt thereof is administered, the effective dosage amounts correspond to the total amount administered.

In one embodiment, the compound of the present invention or a pharmaceutically acceptable salt thereof is administered concurrently with another therapeutic agent.

In one embodiment, a composition comprising an effective amount of a compound of the present invention or a pharmaceutically acceptable salt thereof and an effective amount of another therapeutic agent within the same composition can be administered.

Effective amounts of the other therapeutic agents are well known to those skilled in the art. However, it is well within the skilled artisan's purview to determine the other therapeutic agent's optimal effective amount range. The compound of the present invention or a pharmaceutically acceptable salt thereof and the other therapeutic agent can act additively or, in one embodiment, synergistically. In one embodiment, of the invention, where another therapeutic agent is administered to an animal, the effective amount of the compound of the present invention or a pharmaceutically acceptable salt thereof is less than its effective amount would be where the other therapeutic agent is not administered. In this case, without being bound by theory, it is believed that the compound of the present invention or a pharmaceutically acceptable salt thereof and the other therapeutic agent act synergistically.

In another aspect of the invention, kits that include one or more compounds of the invention are provided. Representative kits include a 5-$HT_6$ inhibitor compound of the invention (e.g., a compound of Formulas I-IV) and a package insert or other labeling including directions for treating a CNS disease by administering an effective amount of a compound of the present invention.

The Scheme shown in Scheme 1 below, and the Preparations following the Scheme describe the procedures used to synthesize the compounds of the present invention. Reasonable variations of the described procedures, which would be evident to one skilled in the art, are intended to be within the scope of the present invention.

Scheme 1
Scheme 1 describes the preparation of compounds of Formula I and intermediates thereof.
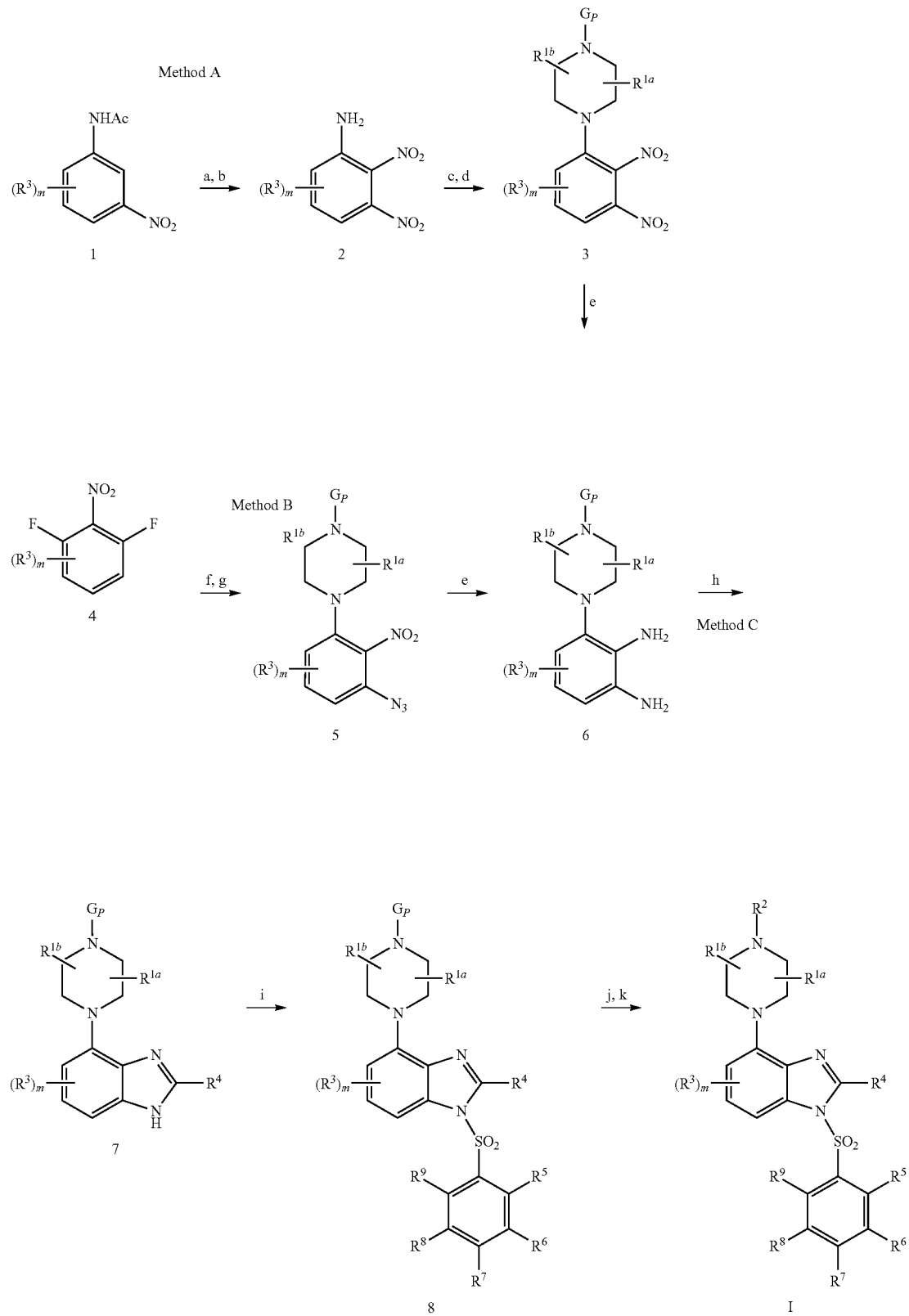

-continued

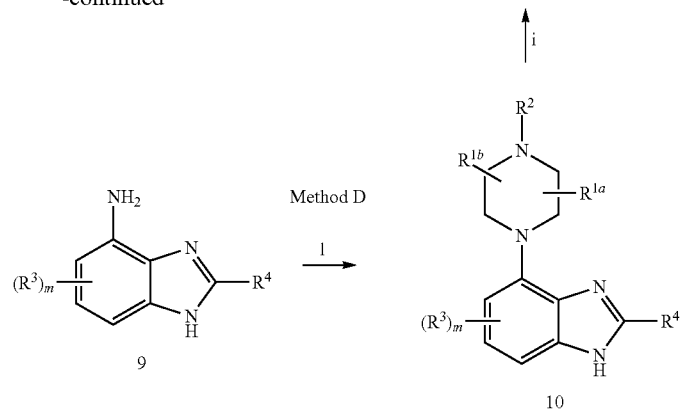

Reagents in each of the steps include: a. HNO₃, H₂SO₄ b. NaOMe, MeOH c. NaNO₂, AcOH, H₂SO₄, CuBr d. Boc-piperazine, BINAP, Pd₂(dba)₃, Cs₂CO₃, toluene. e. H₂/Pd-C 10%, EtOH f. NaN₃, DMSO g. Boc-piperazine, Hunig's Base, DMSO h. R¹C(OEt)₃, montmorillonite KSF, toluane i. R⁵, R⁶, R⁷, R⁸, R⁹, or R¹⁰-substituted aryl-SO₂Cl, NaH, DMF j. TFA, CH₂Cl₂ (when G$_P$ = Boc) k. R²CHO, NaBH(OAc)₃, 1,2-dichloroethane l. bis(2-chloroethyl)-alkylamine, NaHCO₃, 1-butanol, 115° C.

Compounds 6 can be prepared via either method A or method B. In an example of method A, N-(3-nitrophenyl) acetamide was nitrated according to a literature procedure to give 2,3-dinitroaniline (2). Subsequently, compound 2 was converted to 2,3-dinitrobromobenzene with sodium nitrite and copper bromide. The latter intermediate was reacted with Boc-piperazine to give the desired product 3. Reduction of intermediate 3 gave the corresponding aniline 6. Alternatively, compound 6 can be prepared in two steps, as an example from commercially available 2,6-difluoronitrobenzene.

Reaction of compound 4 with sodium azide and Boc-piperazine gave intermediate 5. Subsequent reduction of compound 5 led to the formation of product 6. The benzimidazole core 7 can be prepared under different conditions established in the literature, such as heating compound 6 in toluene in the presence of montmorillonite KSF and triethyl orthoformate. The sulfone intermediate 8 can be prepared from the reaction of compound 7 with the appropriate substituted aryl sulfone. Deprotection and subsequent reductive amination of compound 8 with the appropriate aldehyde gave the desired compounds of Formula I. Alternatively, compounds of Formula I can be prepared from intermediate 10, which in turn results from the reaction of intermediate 9 with bis(2-chloroethyl) alkylamine.

One of skill in the art will recognize that Scheme 1 can be adapted to produce the other compounds of Formulas I-IV and pharmaceutically acceptable salts of compounds of Formulas I-IV according to the present invention.

EXAMPLES

The following abbreviations are used herein and have the indicated definitions: ACN is acetonitrile, AcOH is acetic acid, BINAP is 2,2'-bis(diphenylphosphino)-1,1'-binaphthalene, and BOC is t-butoxycarbonyl. Celite™ is flux-calcined diatomaceous earth. Celite™ is a registered trademark of World Minerals Inc. DMF is N,N-dimethylformamide and DMSO is dimethylsulfoxide. EDTA is ethylenediaminetetraacetic acid, ESI and ES both stand for Electrospray Ionization, EtOAc is ethyl acetate, and EtOH is ethanol. [³H]-LSD is tritium-labeled lysergic acid diethylamide, Hunig's Base is diisopropylethylamine, HPLC is high-pressure liquid chromatography, MeCN is acetonitrile, MeOH is methanol, and MS is mass spectrometry. NMR is nuclear magnetic resonance, PBS is phosphate-buffered saline (pH 7.4), TFA is trifluoroacetic acid, THF is tetrahydrofuran, TLC is thin-layer chromatography and TMS is tetramethylsilane. PVT WGA SPA is polyvinyltoluidene wheat germ agglutinin scintillation proximity assay, Synthetic Methods Each of the following methods corresponds to Scheme 1 shown above, wherein R¹ is H, m is 0, and G$_P$ is Boc. The compounds and/or intermediates were characterized by LC mass spectrometric analysis performed on an Agilent HPLC and a Hewlett-Packard mess spectrometer with an Onyx Monolithic C18 Column (100×3.0 mm): solvent system: 10-100% Acetonitrile in water, flow rate: 1.8 mL/min, molecular weight range 200-700. Nuclear magnetic resonance (NMR) analysis was performed on the compounds with a 400 MHz Varian NMR instrument (Palo Alto, Calif.). The spectral reference is either TMS or the known chemical shift of the solvent. Some compound samples are run at elevated temperatures (e.g., 75° C.) to promote increased sample solubility.

It should be understood that the organic compounds according to the invention may exhibit the phenomenon of tautomerism. As the chemical structures within this specification can only represent one of the possible tautomeric forms, it should be understood that the invention encompasses any tautomeric form of the drawn structure.

Method A: Preparation of 2,3-dinitroaniline (2)

2,3-dinitroaniline can be prepared from N-(2,3-dinitrophenyl)acetamide, which in turn is prepared from the commercial material 3-nitroacetamide as described in the scheme below:

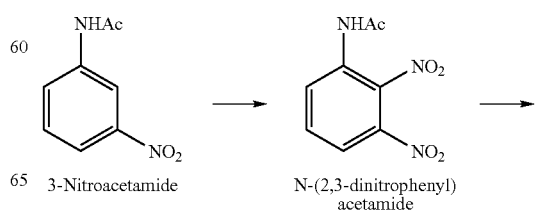

3-Nitroacetamide        N-(2,3-dinitrophenyl)
                              acetamide

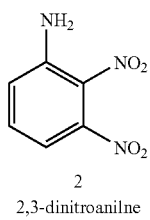

2
2,3-dinitroanilne

A. N-(2,3-dinitrophenyl)acetamide

To a stirring mixture of concentrated sulfuric acid (216 mL) and 90% nitric (fuming) acid (216 mL) cooled at −3° C., was added 3-nitroacetanilide (12.0 g) in portions over 20 minutes. The mixture was stirred for 30 minutes at −10° C. Then the reaction was allowed to warm to room temperature over one hour and poured over crushed ice (600 mL) to give a yellow solid. The resulting precipitate was collected by suction. The solid obtained was dissolved in boiling ethanol (125 mL) and this solution was allowed to sit for 2 hours. The resulting light-yellow needles were filtered, washed with ethanol and air dried to give the desired product (3.1 g, 21%). See Arnold T. Nielsen, Ronald L. Atkins, William P. Norris, Clifford L. Coon, Michael E. Sitzmann J. Org. Chem.; 1980; 45(12); 2341-2347 (incorporated herein by reference). Chemical Formula: $C_8H_7N_3O_5$ Molecular Weight: 225.16; MS (ES) m/z 226.

B. 2,3-dinitroaniline

To a solution of N-(2,3-dinitrophenyl)acetamide (3.0 g) in methanol (200 mL) was added sodium methoxide (72 mg). The stirred solution was heated at reflux for 3 hours. Water was added to the solution (300 mL) and the yellow solid precipitate was collected and dried to give the desired product (2.27 g, 93%). Chemical Formula: $C_6H_5N_3O_4$ Molecular Weight: 183.12; MS (ES) m/z 184

Preparation of tert-butyl 4-(2,3-dinitrophenyl)piperazine-1-carboxylate (3)

Compound 3 can be prepared according to scheme below:

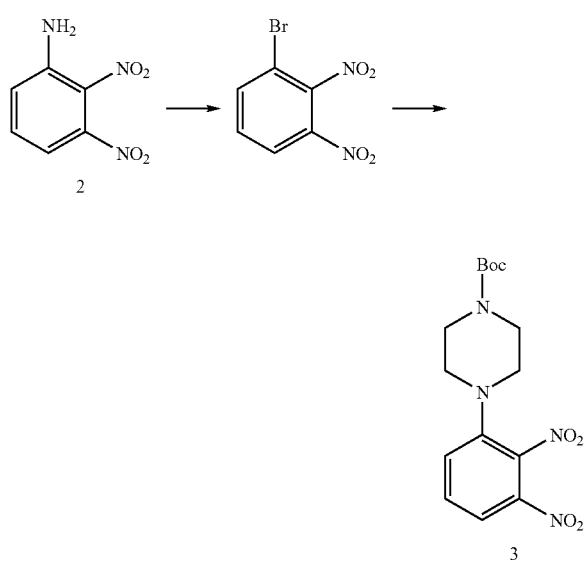

1-bromo-2,3-dinitrobenzene

A solution of 2,3-dinitroaniline (2.27 g, 12.4 mmol) in 35 mL of glacial acetic acid was added dropwise to a stirred and cooled solution of sodium nitrite (0.95 g, 13.8 mmol) in concentrated sulfuric acid (7 mL) while the temperature of the reaction was held at 15-20° C. The resulting diazonium solution was then added over a five minute period to a stirred solution of copper bromide (1.85 g, 12.9 mmol) in a mixture of HBr (48%) (10 mL) and water (10 mL) heated at 75° C.-80° C. After the addition, the mixture was cooled to room temperature and added to water (500 mL). The light-green powder was filtered from the solution and dried in vacuum at room temperature to give the desired product 1-bromo-2,3-dinitrobenzene (3.0 g, 99%). This product was used in subsequent reaction without further purification. See, Donald L. Vivian *J. Org. Chem.* 1956, 21, 1188.

Compound 3

A mixture of 1-bromo-2,3-dinitrobenzene (1.0 g, 4.05 mmol), N-Boc-piperazine (0.90 g, 4.86 mmol), cesium carbonate (1.58 g, 4.86 mmol), BINAP (0.113 g, 0.182 mmol), and tris(dibenzylideneacetone)dipalladium (0.111 g, 0.121 mmol) in toluene (12.0 mL) was heated at reflux for four hours. Toluene was evaporated and the residue was dissolved in dichloromethane (100 mL), washed with water, dried over sodium sulfate, and filtered. The dichloromethane was evaporated and the residue is chromatographed on silica gel using hexane/ethyl acetate (30-70% EtOAc) to give the desired product 3 (0.37 g, 26%). MB (ES) m/z 353. See, Shashank Shekhar, Per Ryberg, John F. Hartwig, Jinu S. Mathew, Donna G. Blackmond, Eric R. Strieter, and Stephen L. Buchwald *J. Am. Chem. Soc.* 2006 128, 3584-3591 (incorporated herein by reference).

Preparation of compound tert-butyl 4-(2,3-diaminophenyl)piperazine-1-carboxylate (6) from compound (3)

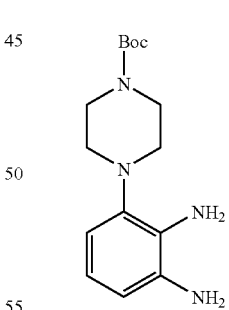

Method A tert-Butyl 4-(2,3-dinitrophenyl)piperazine-1-carboxylate (3) is dissolved in ethanol (8.0 mL) and to this is added 10% Pd—C (30 mg). Hydrogenation of this mixture was completed on a Parr apparatus at 33 psi over night. Mixture is filtered through CELITE™ and chromatographed on a silica gel column using dichloromethane and ethyl acetate (15-50% EtOAc) to yield the desired product as a light brown amorphous solid (0.129 g, 79%); MS (ES) m/z 293

Preparation of tert-butyl 4-(3-azido-2-nitrophenyl)piperazine-1-carboxylate (5)

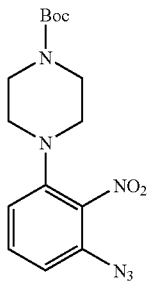

Compound 5 can be prepared from compound 4 according to the following scheme:

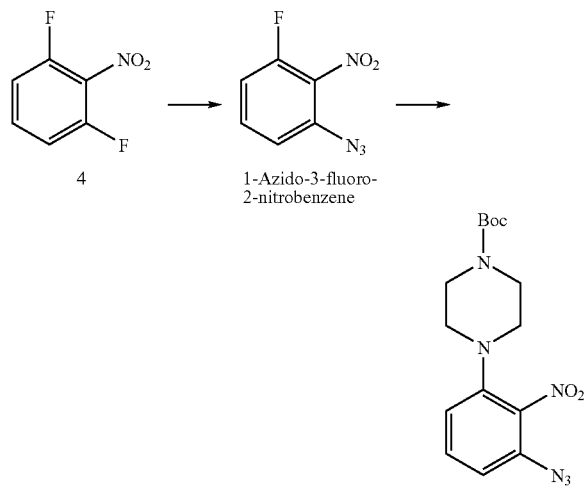

Preparation of 1-Azido-3-fluoro-2-nitrobenzene

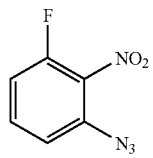

To a stirred solution of 2,6-difluoronitrobenzene (2.0 g, 12.6 mmol) in DMSO (6.0 mL) at room temperature, was added sodium azide (0.82 g; 12.6 mmol). After 18 hours the solution was poured into 200 mL of ice-cold water. The precipitate, 1-azido-3-fluoro-2-nitrobenzene, was collected and dried under vacuum (2.26 g; 99%); $^1$H NMR (CDCl3, 400 MHz) δ 7.00 (t, J=8.8 Hz, 1H); 7.07 (d, J=8.35 Hz, 1H); 7.47 (dt, J=8.35, 5.68 Hz, 1H). MS (ES) m/z 182.1

Preparation of Compound 5

To a solution of 1-azido-3-fluoro-2-nitrobenzene (0.35 g; 1.9 mmol) in DMSO (2.0 mL) was added Boc-piperazine (0.40 mL; 1.2 eq) and N-Boc-piperazine (1.2 eq.). The solution was heated at 60° C. for 6 hours. When the reaction was complete, the solution was poured into water (50 mL) and extracted into ethyl acetate. The organic solution was dried over Na$_2$SO$_4$, filtered, and evaporated under reduced pressure. The residue is chromatographed on silica using dichloromethane/methanol. The purified product 5 is crystallized from diethyl ether and hexane; MS (ES) m/z 348.2;

Preparation of compound tert-butyl 4-(2,3-diaminophenyl)piperazine-1-carboxylate (6) from compound (5) (Method B)

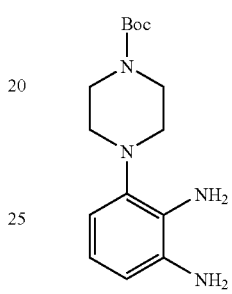

Compound 5 (2.43 g, 6.98 mmol) was suspended in methanol (100 mL) and to this is added 10% Pd—C (0.37 g). Hydrogenation of this mixture was completed on a Parr apparatus at 33 psi over 2 hours. Mixture is filtered through Celite™ and chromatographed on a silica gel column using dichloromethane and ethyl acetate (15-50% EtOAc) to yield the desired product as a light brown amorphous solid (1.97 g, 97%); MS (ES) m/z 293.

Procedures for the preparation of tert-butyl 4-(2-methyl-1 h-benzo[d]imidazol-4-yl)piperazine (7) from compound (6) (Method C)

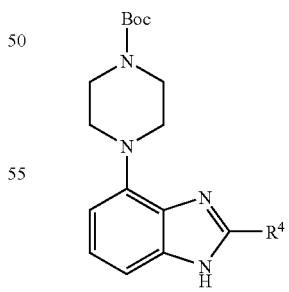

To the phenylene diamine (6) is added triethyl orthoformate and toluene followed by 17 mg of montmorillonite KSF. The mixture is heated at reflux overnight. The toluene is evaporated and the residue is chromatographed on silica using straight ethyl acetate to give the desired product (7).

General procedure for the preparation of tert-butyl 4-(2-alkyl-1-arylsulfonyl)-1H-benzo[d]imidazol-4-yl)piperazine (8) from compound 7

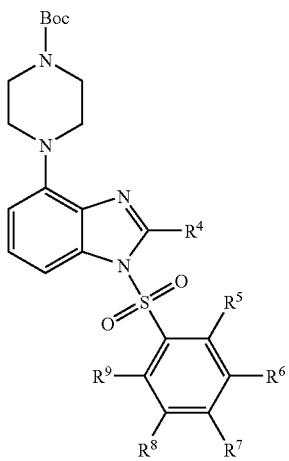

8

To a mixture of a substituted or unsubstituted tert-butyl 4-(2-alkyl-1H-benzo[d]imidazol-4-yl)piperazine (7) in 5 mL of DMF is added sodium hydride (2.0 eq.) at 0° C. The resulting suspension is stirred at room temperature for 30 minutes, followed by the addition of substituted or unsubstituted aryl sulfonylchloride. The mixture is stirred at room temperature until reaction is completed as shown by LC/MS. The solution is poured into 100 mL H₂O and the resulting solid was separated from the solution by suction filtration, and dried under vacuum.

Procedure for the preparation of 2-alkyl-4-(4-alkylpiperazin-1-yl)-1-(arylsulfonyl)-1H-benzo[d]imidazole (I) from compound 8

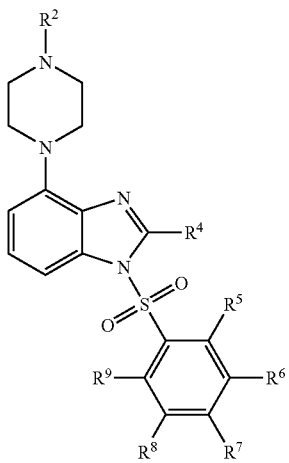

Compound 8 is dissolved in dichloromethane (CH₂Cl₂) followed by the addition of an excess of TFA. The mixture is stirred at room temperature until reaction is completed as shown by LC/MS. The solvent is removed under vacuum and suspended in dichloromethane followed by the addition of sodium potassium carbonate. The reaction mixture is filtered over a pad of Celite™ and the filtrate is reduced under vacuum to give the desired free base product. Where R² is other than H, to the mixture of the free base material in dichloroethane is added an aldehyde (1.20 equiv.) followed by the addition of sodium triacetoxyborohydride (1.6 eq.). The reaction is stirred overnight, solvent is evaporated, and the residue is purified by flash chromatography using dichloromethane/methanol (5-20%).

Procedure for the preparation of 2-alkyl-4-(4-alkylpiperazin-1-yl)-1-(arylsulfonyl)-1H-benzo[d]imidazole (I) from compound (10) Method D Compound of Formula I can alternatively be prepared from intermediate 10 according to the general procedure described for the preparation of compound 8.

Procedure for Preparing Compound (10)

A mixture of 4-aminobenzimidazole, bis(chloroethyl)alkylamine is stirred in 25 mL of 1-butanol with sodium bicarbonate (3.0 equiv.). The mixture was heated at reflux temperature (115° C. oil bath) overnight. The mixture was cooled, filtered through a pad of Celite™ and the filtrate was concentrated under vacuum. The crude residue was purified on a column of silica gel to yield the desired product. See also synthetic methodology provided in: WO 2006/009734; Villemin et al., *Synthetic Communications* 1996 26 (15), 2895-2899; and Marcos et al., Tetrahedron 1991 47(35), 7459-64 (incorporated herein by reference).

Each of the following Example compounds was prepared according to the methodology described above.

Example 1

4-(4-methylpiperazin-1-yl)-1-(naphthalen-1-ylsulfonyl)-1H-benzo[d]imidazole

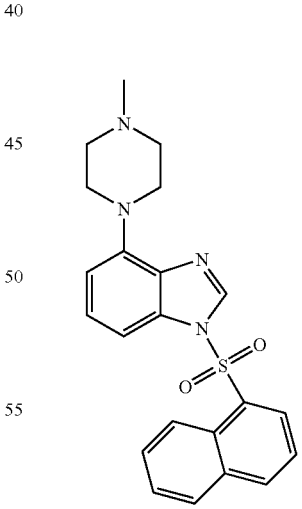

This compound was prepared as described above; MS (ES) m/z 407.15; ¹H NMR (400 MHz, chloroform-d) δ ppm 2.44 (s, 3H) 2.71-2.81 (m, 4H) 3.51-3.59 (m, 4H) 6.67 (dd, J=7.8, 1.3 Hz, 1H) 7.15-7.25 (m, 1H) 7.56-7.65 (m, 2H) 7.65-7.70 (m, 1H) 7.89-7.94 (m, 1H) 8.12-8.17 (m, J=8.4 Hz, 1H) 8.49 (dd, J=7.5, 1.3 Hz, 1H) 8.54 (s, 1H) 8.66 (dd, J=8.7, 0.8 Hz, 2H).

Example 2

1-(naphthalen-1-ylsulfonyl)-4-(piperazin-1-yl)-1H-benzo[d]imidazole

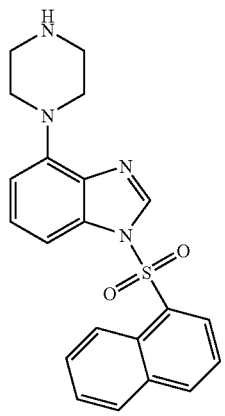

This compound was prepared as described above; MS (ES) m/z 393.13; $^1$H NMR (400 MHz, DMSO-$d_6$) δ ppm 2.79-2.85 (m, 4H); 3.29-3.33 (m, 4H); 3.37-3.43 (m, 1H); 6.61 (dd, J=7.8, 1.0 Hz, 1H); 7.07-7.18 (m, 2H); 7.66-7.72 (m, 1H); 7.74-7.84 (m, 2H); 8.13 (d, J=7.6 Hz, 1H); 8.41 (d, J=8.5 Hz, 1H); 8.64 (dd, J=8.5, 0.7 Hz, 1H); 8.69 (dd, J=7.4, 1.1 Hz, 1H); 9.08 (s, 1 H).

Example 3

1-(phenylsulfonyl)-4-(piperazin-1-yl)-1H-benzo[d]imidazole

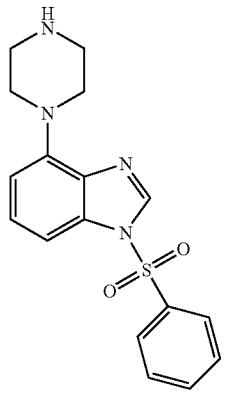

This compound was prepared as described above: MS (ES) m/z 343.12; $^1$H NMR (400 MHz, DMSO-$d_6$) δ ppm 3.24-3.31 (m, 4H); 3.63-3.70 (m, 4H); 6.81 (d, J=7.8 Hz, 1H) 7.31 (t, J=8.1 Hz, 1H) 7.42 (d, J=7.6 Hz, 1H) 7.67 (t, J=7.8 Hz, 2H) 7.78 (tt, J=7.5, 1.2 Hz, 1H) 8.11-8.16 (m, 2H) 8.77 (br. s., 1H) 8.79 (s, 1H).

Example 4

2-methyl-1-(1-naphthylsulfonyl)-4-piperazin-1-yl-1H-benzimidazole

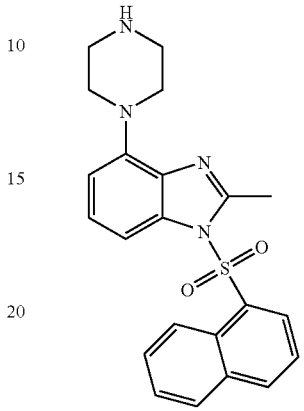

This compound was prepared as described above: MS (ES) m/z 407.0; $^1$H NMR (400 MHz, DMSO-$d_6$) δ ppm 2.69 (s, 3H); 2.79-2.90 (m, 4H); 3.33-3.49 (m, 4H); 3.56-3.63 (m, 1H); 6.67 (d, J=7.8 Hz, 1H); 7.16 (t, J=7.9 Hz, 1H); 7.26 (d, J=8.1 Hz, 1H); 7.69 (dt, J=12.6, 6.6 Hz, 2H); 7.76 (t, J=7.8 Hz, 1H); 8.16 (d, J=7.1 Hz, 1H); 8.24 (d, J=7.1 Hz, 1H); 8.33 (d, J=7.8 Hz, 1H); 8.41 (d, J=8.3 Hz, 1H).

Example 5

2-methyl-1-(phenylsulfonyl)-4-piperazin-1-yl-1H-benzimidazole

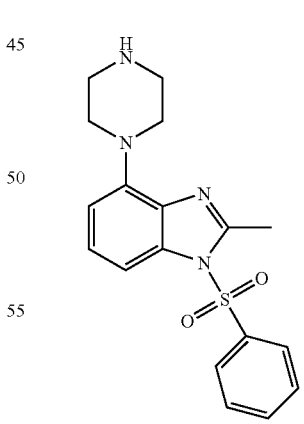

This compound was prepared as described above: MS (ES) m/z 357.0; $^1$H NMR (400 MHz, DMSO-$d_6$) δ ppm 2.78 (s, 3H); 2.81-2.86 (m, 4H); 3.27-3.33 (m, 5H); 6.67 (d, J=8.1 Hz, 1H); 7.19 (t, J=8.2 Hz, 1H); 7.39 (d, J=8.1 Hz, 1H); 7.65 (t, J=7.9 Hz, 2H); 7.77 (t, J=7.4 Hz, 1H); 8.04 (d, J=7.6 Hz, 2H).

Example 6

2-ethyl-1-(phenylsulfonyl)-4-piperazin-1-yl-1H-benzimidazole

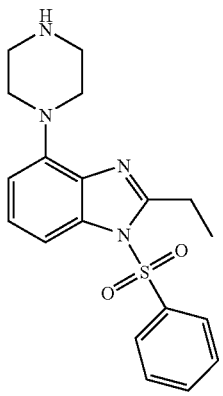

This compound was prepared as described above: MS (ES) m/z 371.1; $^1$H NMR (400 MHz, DMSO-$d_6$) δ ppm 1.30 (t, J=7.3 Hz, 3H); 2.78-2.84 (m, 4H); 3.13 (q, J=7.3 Hz, 2H); 3.22-3.31 (m, 5H); 6.63 (d, J=7.3 Hz, 1H); 7.14 (t, J=8.2 Hz, 1H); 7.35 (dd, J=8.1, 0.7 Hz, 1H); 7.56-7.62 (m, 2H); 7.69-7.74 (m, 1H); 7.94-7.97 (m, 2H).

Example 7

4-(4-ethylpiperazin-1-yl)-1-(phenylsulfonyl)-1H-benzimidazole

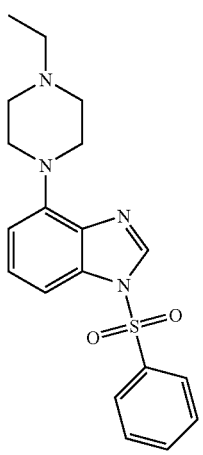

This compound was prepared as described above: MS (ES) m/z 371.1; $^1$H NMR (400 MHz, DMSO-$d_6$) δ ppm 1.27 (t, J=7.3 Hz, 3H); 3.09-3.25 (m, 5H); 3.57 (d, J=11.0 Hz, 2H); 4.34 (d, J=11.2 Hz, 2H); 6.82 (d, J=7.6 Hz, 1H); 7.31 (t, J=8.1 Hz, 1H); 7.43 (d, J=7.8 Hz, 1H); 7.67 (t, J=7.8 Hz, 2H); 7.76-7.81 (m, 1H); 8.12-8.16 (m, J=7.3 Hz, 2H); 8.80 (s, 1H); 10.22 (s, 1H).

Example 8

2-butyl-1-(phenylsulfonyl)-4-piperazin-1-yl-1H-benzimidazole

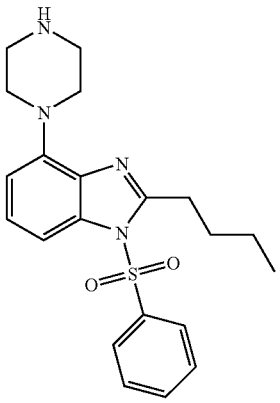

This compound was prepared as described above: MS (ES) m/z 399.1; $^1$H NMR (400 MHz, DMSO-$d_6$) δ ppm 0.92 (t, J=7.4 Hz, 3H); 1.36-1.48 (m, 2H); 1.71-1.82 (m, 2H); 2.81-2.87 (m, 2H); 3.14 (t, J=7.4 Hz, 2H); 3.21-3.26 (m, 2H); 3.33-3.39 (m, 5H); 6.67 (d, J=8.3 Hz, 1H); 7.15-7.21 (m, 1H); 7.36-7.41 (m, 1H); 7.61-7.67 (m, J=7.8, 7.8 Hz, 2H); 7.73-7.79 (m, 1H); 7.96-8.00 (m, 2H).

Example 9

2-methyl-4-(4-methylpiperazin-1-yl)-1-(1-naphthyl-sulfonyl)-1H-benzimidazole

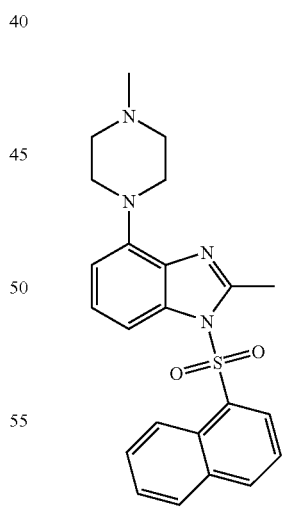

This compound was prepared as described above: MS m/z 421.1; $^1$H NMR (400 MHz, DMSO-$d_6$) δ ppm 2.21 (s, 3H); 2.44-2.49 (m, 4H); 2.69 (s, 3H); 3.37-3.44 (m, 4H); 6.69 (dd, J=8.1, 0.7 Hz, 1H); 7.16 (t, J=8.1 Hz, 1H); 7.27 (dd, J=8.3, 0.7 Hz, 1H); 7.66-7.73 (m, 2H); 7.74-7.79 (m, 1H); 8.14-8.18 (m, 1H); 8.25 (dd, J=7.6, 1.0 Hz, 1H); 8.31-8.34 (m, J=7.8 Hz, 1H); 8.41 (d, J=8.3 Hz, 1H).

Example 10

1-[(4-chlorophenyl)sulfonyl]-4-piperazin-1-yl-1H-benzimidazole

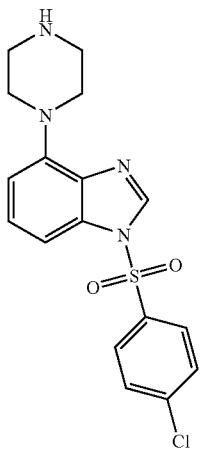

This compound was prepared as described above: MS (ES) m/z 377.1; $^1$H NMR (400 MHz, DMSO-$d_6$) δ ppm 2.82-2.87 (m, 4H); 3.33-3.37 (m, 5H); 6.70 (dd, J=7.7, 1.1 Hz, 1H); 7.25 (t, J=7.9 Hz, 1H); 7.28-7.31 (m, 1H); 7.74 (dt, J=9.2, 2.5 Hz, 2H); 8.14 (dt, J=9.1, 2.5 Hz, 2H); 8.70 (s, 1H).

Example 11

1-[(2-chlorophenyl)sulfonyl]-4-piperazin-1-yl-1H-benzimidazole

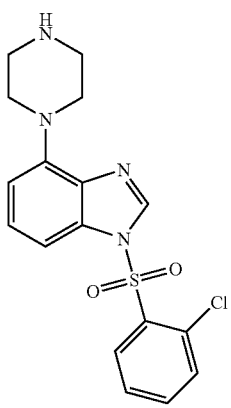

This compound was prepared as described above: MS (ES) m/z 377.1; $^1$H NMR (400 MHz, DMSO-$d_6$) δ ppm 2.84-2.90 (m, 4H); 3.35-3.44 (m, 5H); 6.69 (d, J=8.1 Hz, 1H); 6.97 (d, J=8.1 Hz, 1H); 7.17 (t, J=8.1 Hz, 1H); 7.68-7.75 (m, 2H); 7.77-7.84 (m, 1H); 8.46 (dd, J=7.8, 1.2 Hz, 1H); 8.75 (s, 1H).

Example 12

4-(4-methylpiperazin-1-yl)-1-(phenylsulfonyl)-1H-benzimidazole

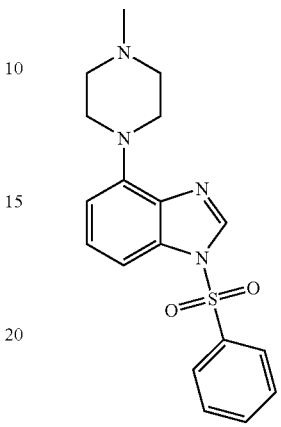

This compound was prepared as described above: MS (ES) m/z 357.1; $^1$H NMR (400 MHz, chloroform-d) δ ppm 2.37 (s, 3H) 2.63-2.69 (m, 4H) 3.50-3.57 (m, 4H) 6.72 (dd, J=8.1, 0.9 Hz, 1H) 7.24-7.30 (m, 1H) 7.42 (dd, J=8.3, 0.9 Hz, 1H) 7.47-7.54 (m, 2H) 7.62 (tt, J=7.4, 1.2 Hz, 1H) 7.95-8.00 (m, 2H) 8.29 (s, 1H)

Biological Assay:

5-HT$_6$ Binding Affinity

CHO-Dukx-A2 cells expressing the serotonin 5-HT$_6$ receptor subtype (clone 50-7) grown adherently in 10-cell stacks are detached and harvested in PBS buffer containing 5 mM EDTA using conventional cell harvesting protocols, followed by centrifugation at 2000 rpms for 10 min (supernatant discarded) or provided as wet cell pellets by Applied Cell Sciences (Rockville, Md.). The pellets are gently resuspended with enough PBS buffer containing MgCl$_2$ and CaCl$_2$, (GIBCO 14040-133) to achieve a final concentration of ~40×10$^6$ cells/ml. The cell suspension is aliquoted into microfuge tubes, centrifuged at 2000 rpms for 10 min, supernatant discarded and stored as dry pellets at −80° C. Protein is measured in 5 μl lysate mixed with 200 μl diluted Bradford reagent, using Bovine Plasma Gamma globulin as a standard.

Binding experiments are performed in a total volume of 200 μl using a 96 well microtiter plate format (Packard Optiplate). On the day of the assay, the cells were thawed and resuspended with enough assay buffer (i.e. PBS containing MgCl$_2$ and CaCl$_2$, (GIBCO 14040-133) supplemented with additional MgCl$_2$ to achieve a final concentration of 10 mM) to achieve 40-80 μg or 100-200 K cells/well. To each well of the microtiter plate, 20 μl of 10× test compound in water containing 3.3% DMSO, 3 nM of [$^3$H]-LSD (GE, SA: 80 Ci/mmol), cells and assay buffer are combined to achieve a volume of 150 Assay buffer and 10 μM cold methiothepin are substituted for the test compound in separate wells to define 'total' and 'nonspecific' binding, respectively. The incubation period is initiated by the addition of 50 μl of 10 mg/ml PVT WGA SPA beads (RPNQ0060, Amersham GE Healthcare) mixed in assay buffer for a final concentration of 1 mg/well. The plates are sealed and gently shaken at room temperature using an orbital shaker (setting 1.5) until equilibrium is achieved (2-6 hours). Radioactivity (CPM) is measured by Packard TopCount (1 min counting time/well).

Specific binding is described as the total radioactivity bound less the amount bound in the presence of 10 μM methiothepin, referred to as nonspecific binding (NSB). Binding in the presence of varying concentrations of test compounds is expressed as percent of specific binding in the absence of compound:

$$\{(Bound-NSB)/(Total-NSB)\} \times 100 = \% \text{ Total}$$

Regression analysis of % bound data from ten concentrations is performed in GraphPad Prism, XL Fit or equivalent software. $IC_{50}$ values are calculated using a four-parameter logistic curve fitting model and Ki values are calculated by the Cheng-Prusoff equation below:

$$Ki = IC_{50}/(1+L/Kd)$$

where L is the nM concentration of the radioactive ligand used and the Kd is the dissociation constant of the ligand for the receptor. The Kd for [$^3$H]-LSD in the SPA binding format is ~3 nM.

Referring to the examples that follow, compounds of the present invention were synthesized using the methods described herein, or other methods, which are known in the art. The compounds in the Table 1 were prepared as described above and screened for 5-HT$_6$ binding activity according to the above Biological Assay.

TABLE 1

| Ex. | Structure | Name | MS (ES) m/z | 5-HT$_6$ binding Ki (nM) |
| --- | --- | --- | --- | --- |
| 1 | 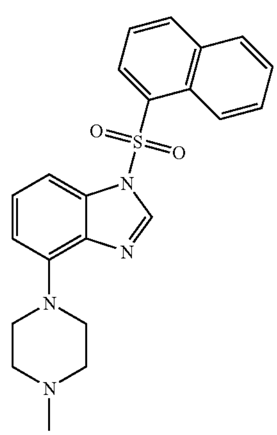 | 4-(4-methylpiperazin-1-yl)-1-(naphthalen-1-ylsulfonyl)-1H-benzo[d]imidazole | 407.15 | 0.064 |
| 2 | 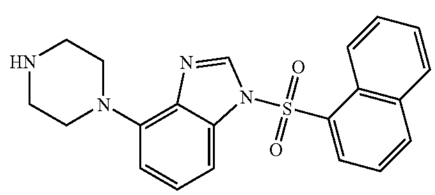 | 1-(naphthalen-1-ylsulfonyl)-4-(piperazin-1-yl)-1H-benzo[d]imidazole | 393.13 | 0.165 |
| 3 | 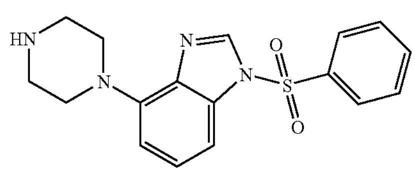 | 1-(phenylsulfonyl)-4-(piperazin-1-yl)-1H-benzo[d]imidazole | 343.12 | 1.36 |
| 4 | 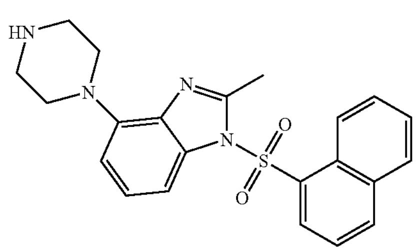 | 2-methyl-1-(1-naphthylsulfonyl)-4-piperazin-1-yl-1H-benzimidazole | 407.0 | 0.025 |

TABLE 1-continued

| Ex. | Structure | Name | MS (ES) m/z | 5-HT$_6$ binding Ki (nM) |
|---|---|---|---|---|
| 5 | 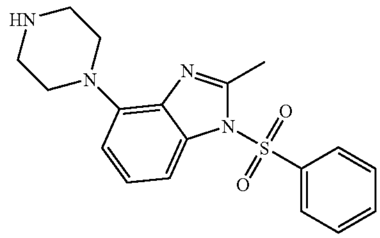 | 2-methyl-1-(phenylsulfonyl)-4-piperazin-1-yl-1H-benzimidazole | 357.0 | 0.53 |
| 6 | 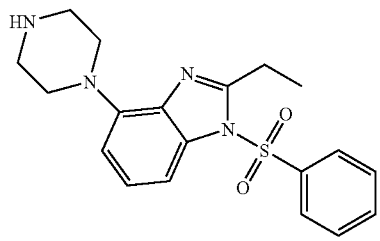 | 2-ethyl-1-(phenylsulfonyl)-4-piperazin-1-yl-1H-benzimidazole | 371.1 | 0.447 |
| 7 | 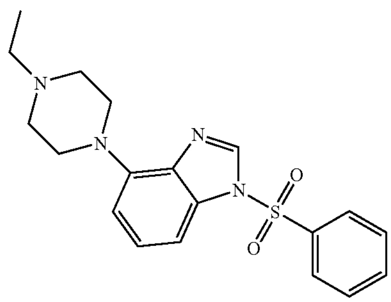 | 4-(4-ethylpiperazin-1-yl)-1-(phenylsulfonyl)-1H-benzimidazole | 371.1 | 0.394 |
| 8 | 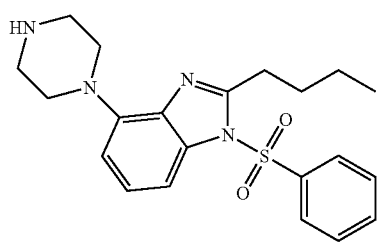 | 2-butyl-1-(phenylsulfonyl)-4-piperazin-1-yl-1H-benzimidazole | 399.1 | 1.10 |
| 9 | 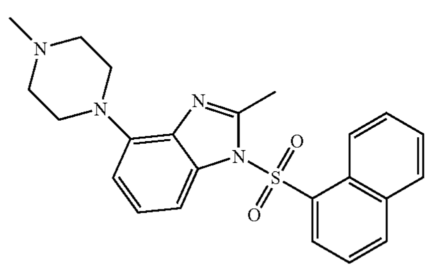 | 2-methyl-4-(4-methylpiperazin-1-yl)-1-(1-naphthylsulfonyl)-1H-benzimidazole | 421.1 | 0.004 |
| 10 | 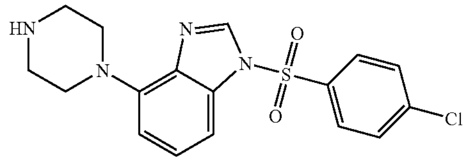 | 1-[(4-chlorophenyl)sulfonyl]-4-piperazin-1-yl-1H-benzimidazole | 377.1 | 1.32 |

TABLE 1-continued

| Ex. | Structure | Name | MS (ES) m/z | 5-HT$_6$ binding Ki (nM) |
|---|---|---|---|---|
| 11 | 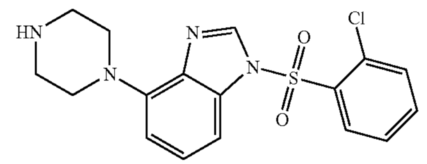 | 1-[(2-chlorophenyl)sulfonyl]-4-piperazin-1-yl-1H-benzimidazole | 377.1 | 0.269 |
| 12 | 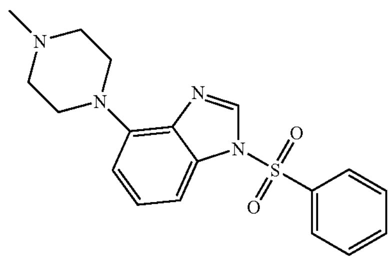 | 4-(4-methylpiperazin-1-yl)-1-(phenylsulfonyl)-1H-benzimidazole | 357.1 | 1.66 |
| 13 | 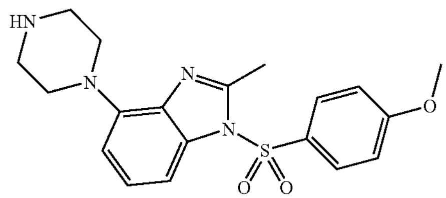 | 1-[(4-methoxyphenyl)sulfonyl]-2-methyl-4-piperazin-1-yl-1H-benzimidazole | 387.1 | 1.82 |
| 14 | 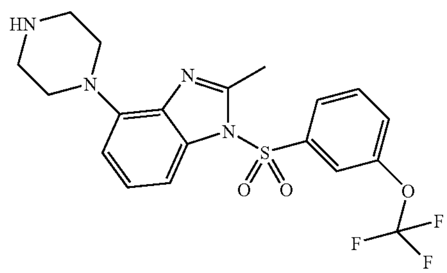 | 2-methyl-4-piperazin-1-yl-1-{[3-(trifluoromethoxy)phenyl]sulfonyl}-1H-benzimidazole | 441.1 | 2.30 |
| 15 | 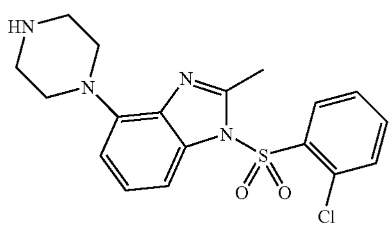 | 1-[(2-chlorophenyl)sulfonyl]-2-methyl-4-piperazin-1-yl-1H-benzimidazole | 391.1 | 0.99 |
| 16 | 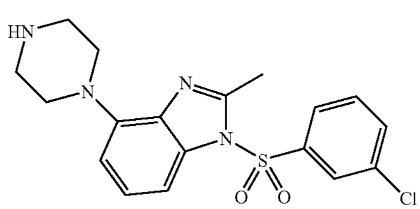 | 1-[(3-chlorophenyl)sulfonyl]-2-methyl-4-piperazin-1-yl-1H-benzimidazole | 391.1 | 0.99 |
| 17 | 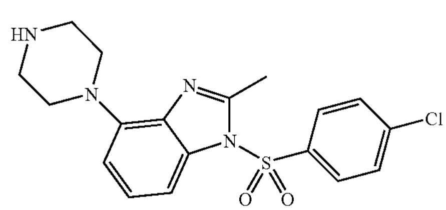 | 1-[(4-chlorophenyl)sulfonyl]-2-methyl-4-piperazin-1-yl-1H-benzimidazole | 391.1 | 6.00 |

TABLE 1-continued

| Ex. | Structure | Name | MS (ES) m/z | 5-HT$_6$ binding Ki (nM) |
|---|---|---|---|---|
| 18 | 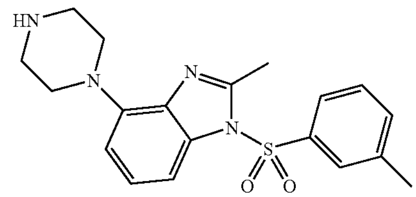 | 2-methyl-1-[(3-methylphenyl)sulfonyl]-4-piperazin-1-yl-1H-benzimidazole | 371.1 | 1.3 |
| 19 | 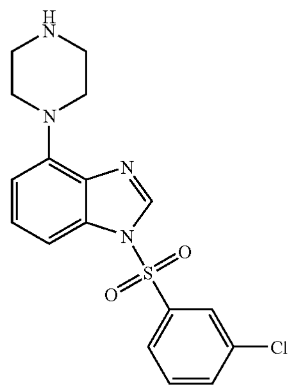 | 1-[(3-chlorophenyl)sulfonyl]-4-piperazin-1-yl-1H-benzimidazole | 377.1 | 4.3 |
| 20 | 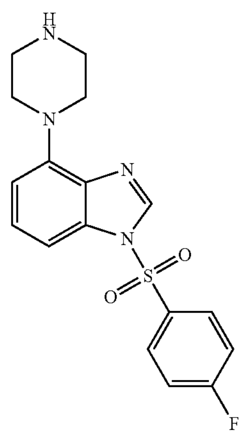 | 1-[(4-fluorophenyl)sulfonyl]-4-piperazin-1-yl-1H-benzimidazole | 361.1 | 25.0 |
| 21 | 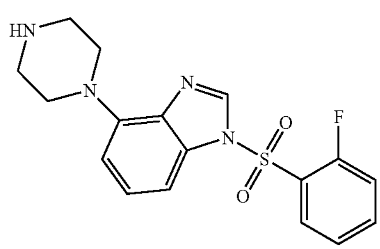 | 1-[(2-fluorophenyl)sulfonyl]-4-piperazin-1-yl-1H-benzimidazole | 361.1 | 3.0 |
| 22 | 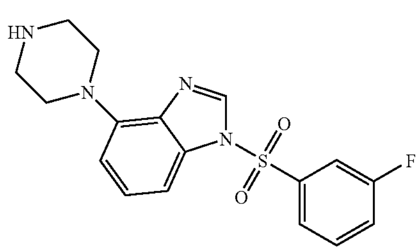 | 1-[(3-fluorophenyl)sulfonyl]-4-piperazin-1-yl-1H-benzimidazole | 361.1 | 1.5 |

TABLE 1-continued

| Ex. | Structure | Name | MS (ES) m/z | 5-HT$_6$ binding Ki (nM) |
|---|---|---|---|---|
| 23 | 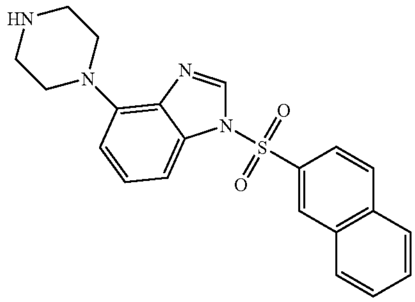 | 1-(2-naphthylsulfonyl)-4-piperazin-1-yl-1H-benzimidazole | 393.1 | 10.6 |
| 24 | 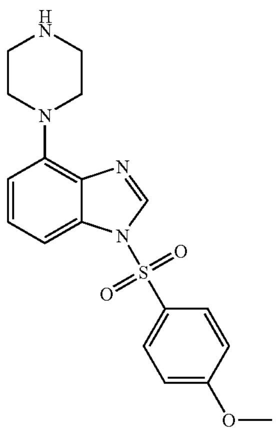 | 1-[(4-methoxyphenyl)sulfonyl]-4-piperazin-1-yl-1H-benzimidazole | 373.1 | 15.1 |
| 25 | 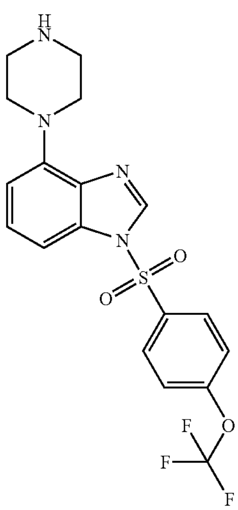 | 4-piperazin-1-yl-1-{[4-(trifluoromethoxy)phenyl]sulfonyl}-1H-benzimidazole | 427.1 | 89.0 |
| 26 | 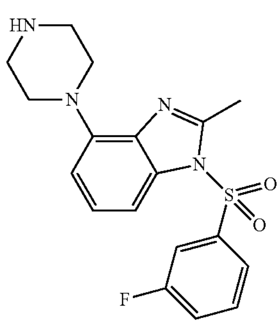 | 1-[(3-fluorophenyl)sulfonyl]-2-methyl-4-piperazin-1-yl-1H-benzimidazole | 375.1 | 1.7 |

TABLE 1-continued
| Ex. | Structure | Name | MS (ES) m/z | 5-HT$_6$ binding Ki (nM) |
|---|---|---|---|---|
| 27 | 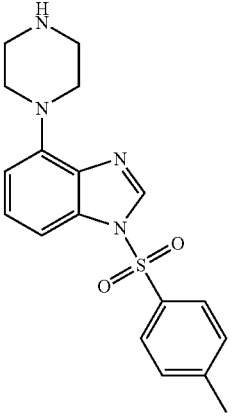 | 1-[(4-methylphenyl)sulfonyl]-4-piperazin-1-yl-1H-benzimidazole | 357.1 | 2.50 |
| 28 | 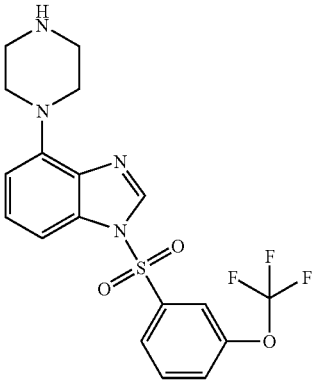 | 4-piperazin-1-yl-1-{[3-(trifluoromethoxy)phenyl]sulfonyl}-1H-benzimidazole | 427.1 | 1.95 |
| 29 | 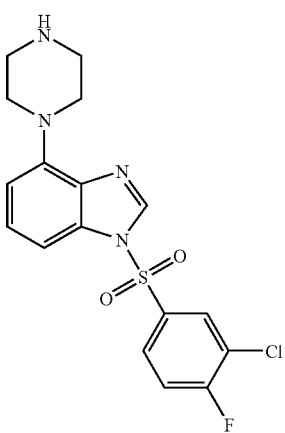 | 1-[(3-chloro-4-fluorophenyl)sulfonyl]-4-piperazin-1-yl-1H-benzimidazole | 395.0 | 11.7 |

TABLE 1-continued

| Ex. | Structure | Name | MS (ES) m/z | 5-HT$_6$ binding Ki (nM) |
|---|---|---|---|---|
| 30 | 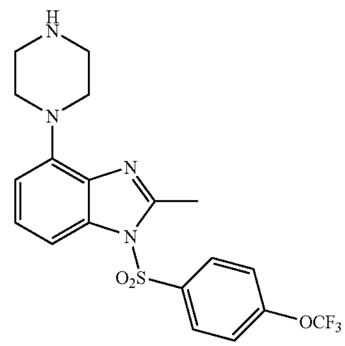 | 2-methyl-4-piperazin-1-yl-1-{[4-(trifluoromethoxy)phenyl]sulfonyl}-1H-benzimidazole | 441.1 | 15.8 |
| 31 | 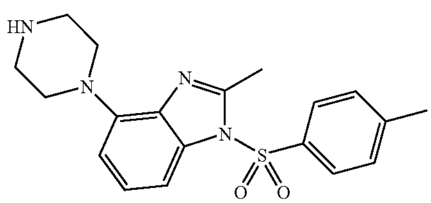 | 2-methyl-1-[(4-methylphenyl)sulfonyl]-4-piperazin-1-yl-1H-benzimidazole | 371.1 | 0.467 |
| 32 | 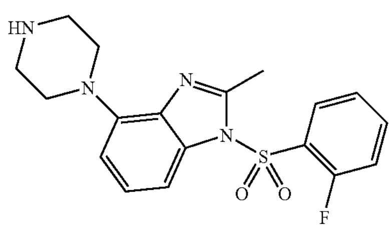 | 1-[(2-fluorophenyl)sulfonyl]-2-methyl-4-piperazin-1-yl-1H-benzimidazole | 375.1 | 2.50 |
| 33 | 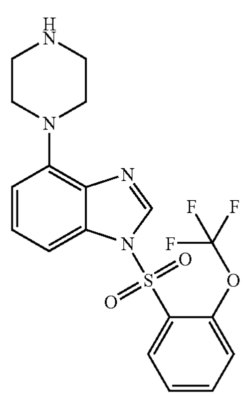 | 4-piperazin-1-yl-1-{[2-(trifluoromethoxy)phenyl]sulfonyl}-1H-benzimidazole | 427.1 | 0.72 |

TABLE 1-continued

| Ex. | Structure | Name | MS (ES) m/z | 5-HT$_6$ binding Ki (nM) |
|---|---|---|---|---|
| 34 | 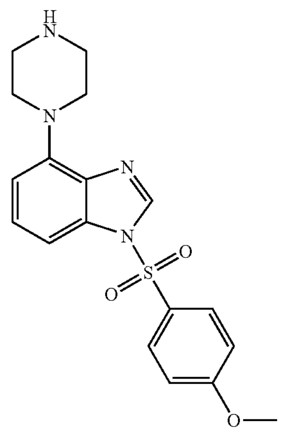 | 1-[(3-methoxyphenyl)sulfonyl]-4-piperazin-1-yl-1H-benzimidazole | 373.1 | 1.20 |
| 35 | 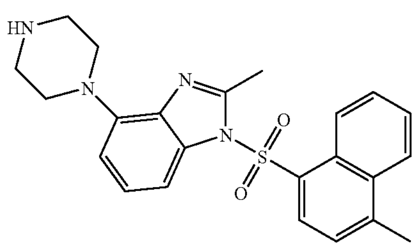 | 1-[(4-methyl-1-naphthyl)sulfonyl]-4-piperazin-1-yl-1H-benzimidazole | 407.1 | 1.10 |
| 36 | 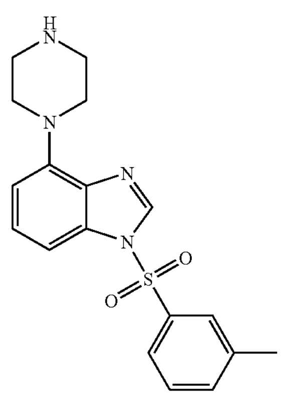 | 1-[(3-methylphenyl)sulfonyl]-4-piperazin-1-yl-1H-benzimidazole | 357.1 | 1.11 |
| 37 | 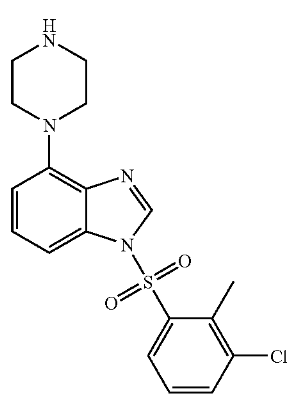 | 1-[(3-chloro-2-methylphenyl)sulfonyl]-4-piperazin-1-yl-1H-benzimidazole | 391.1 | 1.4 |

TABLE 1-continued

| Ex. | Structure | Name | MS (ES) m/z | 5-HT$_6$ binding Ki (nM) |
|---|---|---|---|---|
| 38 | 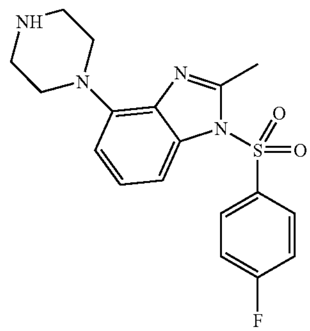 | 1-[(4-fluorophenyl)sulfonyl]-2-methyl-4-piperazin-1-yl-1H-benzimidazole | 375.1 | 10.5 |
| 39 | 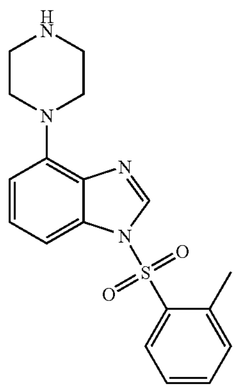 | 1-[(2-methylphenyl)sulfonyl]-4-piperazin-1-yl-1H-benzimidazole | 357.1 | 1.15 |
| 40 | 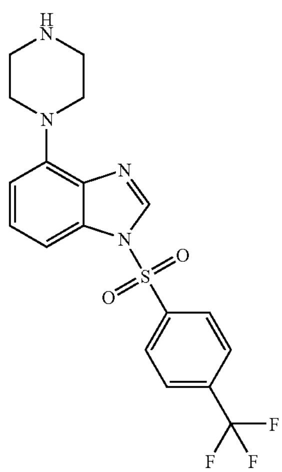 | 4-piperazin-1-yl-1-{[4-(trifluoromethyl)phenyl]sulfonyl}-1H-benzimidazole | 411.1 | 18.9 |
| 41 | 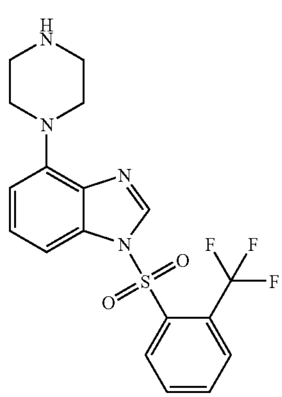 | 4-piperazin-1-yl-1-{[2-(trifluoromethyl)phenyl]sulfonyl}-1H-benzimidazole | 411.1 | 1.06 |

TABLE 1-continued

| Ex. | Structure | Name | MS (ES) m/z | 5-HT$_6$ binding Ki (nM) |
|---|---|---|---|---|
| 42 | 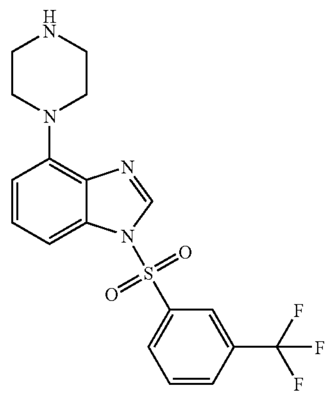 | 4-piperazin-1-yl-1-{[3-(trifluoromethyl)phenyl]sulfonyl}-1H-benzimidazole | 411.1 | 1.13 |
| 43 | 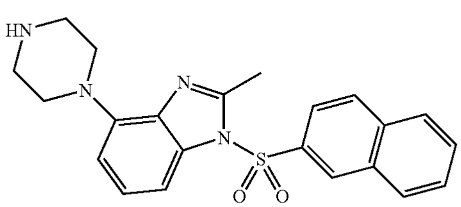 | 2-methyl-1-(2-naphthylsulfonyl)-4-piperazin-1-yl-1H-benzimidazole | 407.1 | 1.05 |
| 44 | 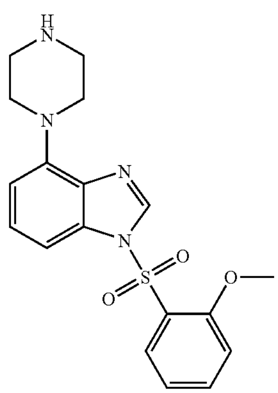 | 1-[(2-methoxyphenyl)sulfonyl]-4-piperazin-1-yl-1H-benzimidazole | 373.1 | 0.156 |
| 45 | 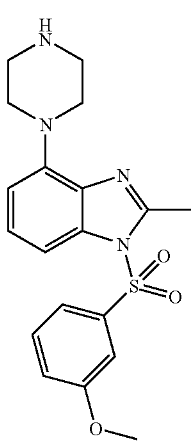 | 1-[(3-methoxyphenyl)sulfonyl]-2-methyl-4-piperazin-1-yl-1H-benzimidazole | 387.1 | 2.07 |

TABLE 1-continued

| Ex. | Structure | Name | MS (ES) m/z | 5-HT$_6$ binding Ki (nM) |
|---|---|---|---|---|
| 46 | 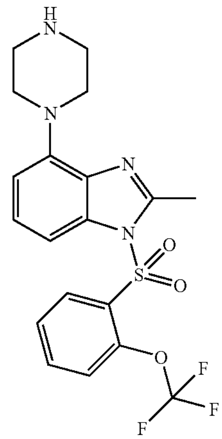 | 2-methyl-4-piperazin-1-yl-1-{[2-(trifluoromethoxy)phenyl]sulfonyl}-1H-benzimidazole | 441.1 | 1.74 |
| 47 | 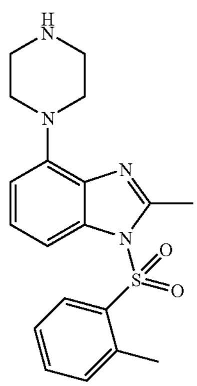 | 2-methyl-1-[(2-methylphenyl)sulfonyl]-4-piperazin-1-yl-1H-benzimidazole | 371.1 | 2.26 |
| 48 | 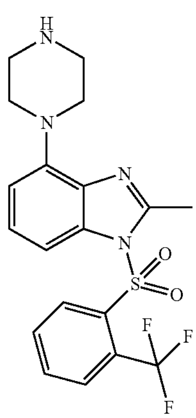 | 2-methyl-4-piperazin-1-yl-1-{[2-(trifluoromethyl)phenyl]sulfonyl}-1H-benzimidazole | 425.1 | 2.94 |

TABLE 1-continued

| Ex. | Structure | Name | MS (ES) m/z | 5-HT$_6$ binding Ki (nM) |
|---|---|---|---|---|
| 49 | 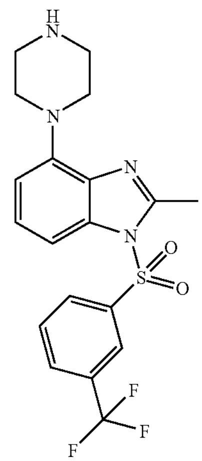 | 2-methyl-4-piperazin-1-yl-1-{[3-(trifluoromethyl)phenyl]sulfonyl}-1H-benzimidazole | 425.1 | 0.982 |
| 50 | 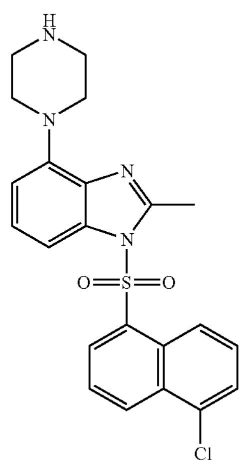 | 1-[(5-chloro-1-naphthyl)sulfonyl]-4-piperazin-1-yl-1H-benzimidazole | 427.1 | 1.36 |
| 51 | 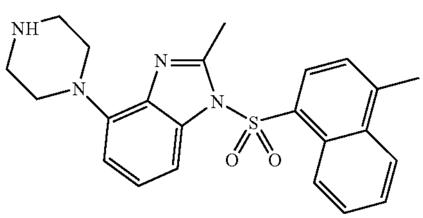 | 2-methyl-1-[(4-methyl-1-naphthyl)sulfonyl]-4-piperazin-1-yl-1H-benzimidazole | 421.1 | 6.27 |
| 52 | 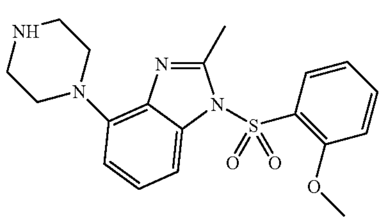 | 1-[(2-methoxyphenyl)sulfonyl]-2-methyl-4-piperazin-1-yl-1H-benzimidazole | 387.1 | 1.89 |

TABLE 1-continued

| Ex. | Structure | Name | MS (ES) m/z | 5-HT$_6$ binding Ki (nM) |
|---|---|---|---|---|
| 53 | 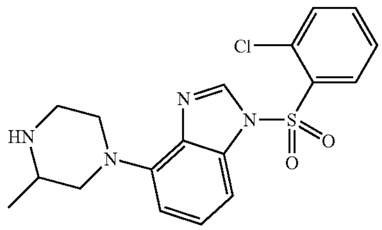 | 1-[(2-chlorophenyl)sulfonyl]-4-(3-methylpiperazin-1-yl)-1H-benzimidazole | 391.1 | 1.34 |
| 54 | 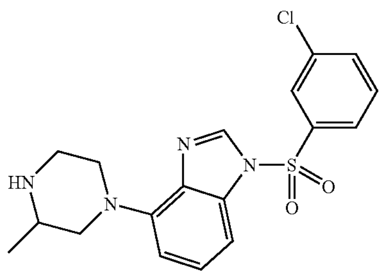 | 1-[(3-chlorophenyl)sulfonyl]-4-(3-methylpiperazin-1-yl)-1H-benzimidazole | 391.0 | 1.92 |
| 55 | 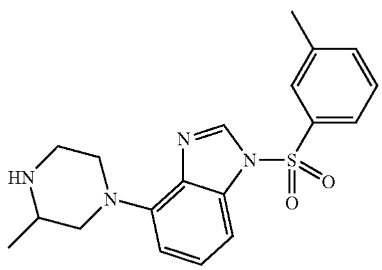 | 1-[(3-methylphenyl)sulfonyl]-4-(3-methylpiperazin-1-yl)-1H-benzimidazole | 371.1 | 2.47 |
| 56 | 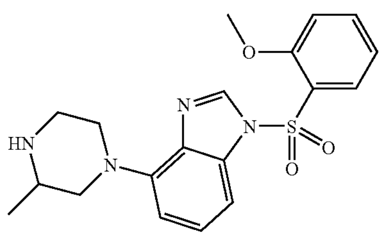 | 1-[(2-methoxyphenyl)sulfonyl]-4-(3-methylpiperazin-1-yl)-1H-benzimidazole | 387.1 | 2.35 |
| 57 | 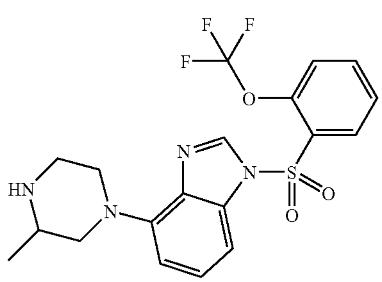 | 4-(3-methylpiperazin-1-yl)-1-{[2-(trifluoromethoxy)phenyl]sulfonyl}-1H-benzimidazole | 441.1 | 2.09 |
| 58 | 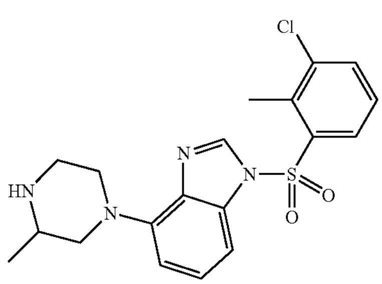 | 1-[(3-chloro-2-methylphenyl)sulfonyl]-4-(3-methylpiperazin-1-yl)-1H-benzimidazole | 405.1 | 1.73 |

TABLE 1-continued

| Ex. | Structure | Name | MS (ES) m/z | 5-HT$_6$ binding Ki (nM) |
|---|---|---|---|---|
| 59 | 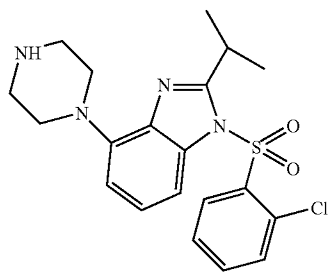 | 1-[(2-chlorophenyl)sulfonyl]-4-(1-methylethyl)-4-piperazin-1-yl-1H-benzimidazole | 419.1 | 0.463 |
| 60 | 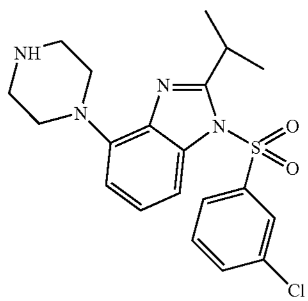 | 1-[(3-chlorophenyl)sulfonyl]-4-(1-methylethyl)-4-piperazin-1-yl-1H-benzimidazole | 419.1 | 1.08 |
| 61 | 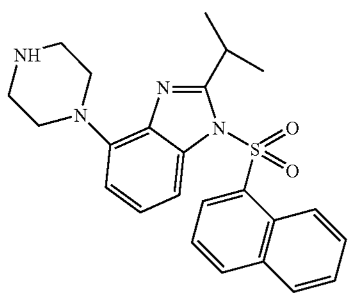 | 2-(1-methylethyl)-1-(naphthalen-1-ylsulfonyl)-4-piperazin-1-yl-1H-benzimidazole | 435.2 | 0.6 |
| 62 | 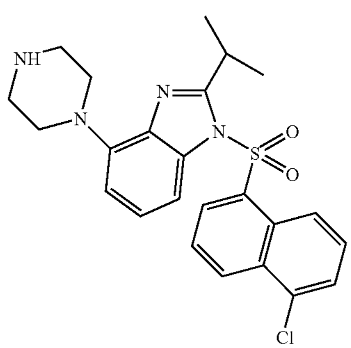 | 1-[(5-chloronaphthalen-1-yl)sulfonyl]-2-(1-methylethyl)-4-piperazin-1-yl-1H-benzimidazole | 469.1 | 1.47 |
| 63 | 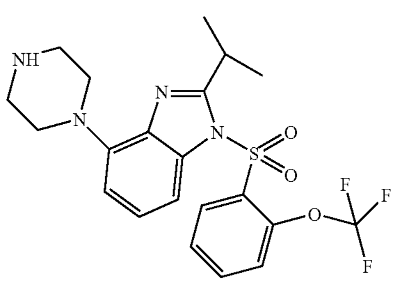 | 2-(1-methylethyl)-4-piperazin-1-yl-1-{[2-(trifluoromethoxy)phenyl]sulfonyl}-1H-benzimidazole | 469.1 | 1.14 |

TABLE 1-continued

| Ex. | Structure | Name | MS (ES) m/z | 5-HT$_6$ binding Ki (nM) |
|---|---|---|---|---|
| 64 | 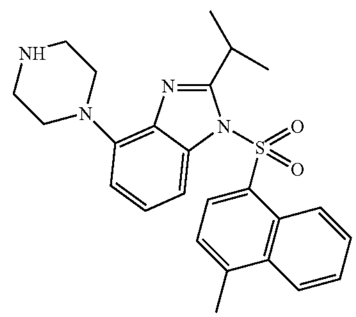 | 2-(1-methylethyl)-1-[(4-methylnaphthalen-1-yl)sulfonyl]-4-piperazin-1-yl-1H-benzimidazole | 449.2 | 1.6 |
| 65 | 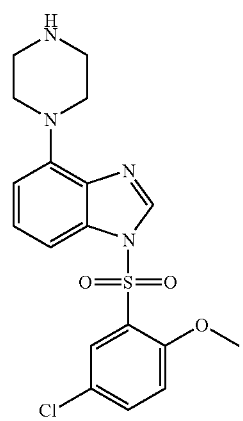 | 1-[(5-chloro-2-methoxyphenyl)sulfonyl]-4-piperazin-1-yl-1H-benzimidazole | 407.1 | 3.56 |
| 66 | 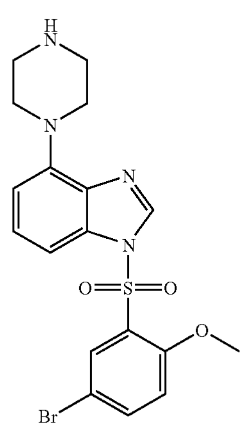 | 1-[(5-bromo-2-methoxyphenyl)sulfonyl]-4-piperazin-1-yl-1H-benzimidazole | 451.0 | 4.93 |

TABLE 1-continued

| Ex. | Structure | Name | MS (ES) m/z | 5-HT$_6$ binding Ki (nM) |
|---|---|---|---|---|
| 67 | 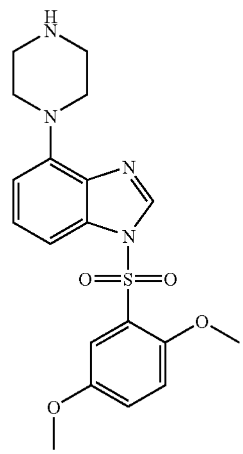 | 1-[(2,5-dimethoxyphenyl)sulfonyl]-4-piperazin-1-yl-1H-benzimidazole | 403.1 | 2.13 |
| 68 | 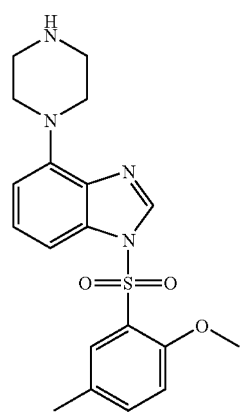 | 1-[(2-methoxy-5-methylphenyl)sulfonyl]-4-piperazin-1-yl-1H-benzimidazole | 387.1 | 0.498 |
| 69 | 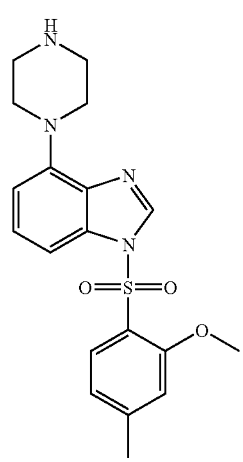 | 1-[(2-methoxy-4-methylphenyl)sulfonyl]-4-piperazin-1-yl-1H-benzimidazole | 387.1 | 2.15 |

TABLE 1-continued

| Ex. | Structure | Name | MS (ES) m/z | 5-HT$_6$ binding Ki (nM) |
|---|---|---|---|---|
| 70 | 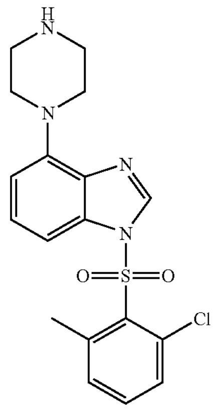 | 1-[(2-chloro-6-methylphenyl)sulfonyl]-4-piperazin-1-yl-1H-benzimidazole | 391.1 | 2.33 |
| 71 | 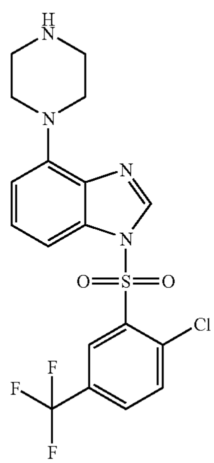 | 1-{[2-chloro-5-(trifluoromethyl)phenyl]sulfonyl}-4-piperazin-1-yl-1H-benzimidazole | 445.0 | 13.7 |
| 72 | 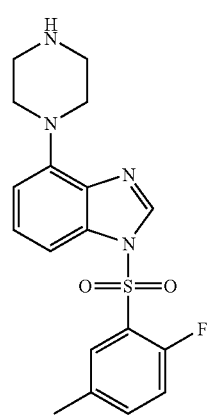 | 1-[(2-fluoro-5-methylphenyl)sulfonyl]-4-piperazin-1-yl-1H-benzimidazole | 375.1 | 0.254 |

TABLE 1-continued

| Ex. | Structure | Name | MS (ES) m/z | 5-HT$_6$ binding Ki (nM) |
|---|---|---|---|---|
| 73 | 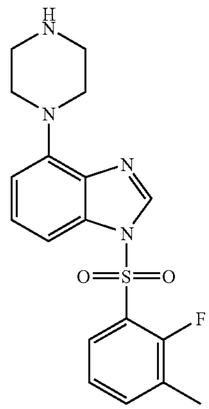 | 1-[(2-fluoro-3-methylphenyl)sulfonyl]-4-piperazin-1-yl-1H-benzimidazole | 375.1 | 0.202 |
| 74 | 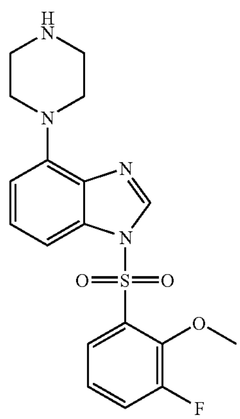 | 1-[(3-fluoro-2-methoxyphenyl)sulfonyl]-4-piperazin-1-yl-1H-benzimidazole | 391.1 | 0.485 |
| 75 | 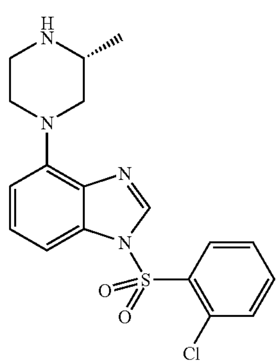 | 1-[(2-chlorophenyl)sulfonyl]-4-[(3R)-3-methylpiperazin-1-yl]-1H-benzimidazole | 391.1 | 1.19 |
| 76 | 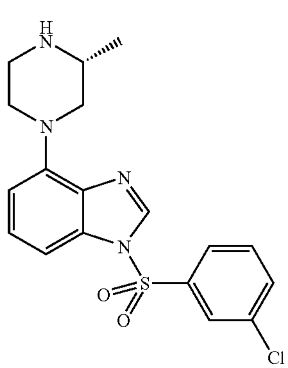 | 1-[(3-chlorophenyl)sulfonyl]-4-[(3R)-3-methylpiperazin-1-yl]-1H-benzimidazole | 391.1 | 2.35 |

TABLE 1-continued

| Ex. | Structure | Name | MS (ES) m/z | 5-HT$_6$ binding Ki (nM) |
|---|---|---|---|---|
| 77 | 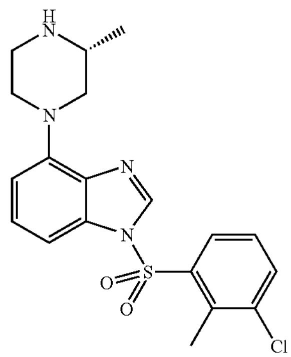 | 1-[(3-chloro-2-methylphenyl)sulfonyl]-4-[(3R)-3-methylpiperazin-1-yl]-1H-benzimidazole | 405.1 | 1.2 |
| 78 | 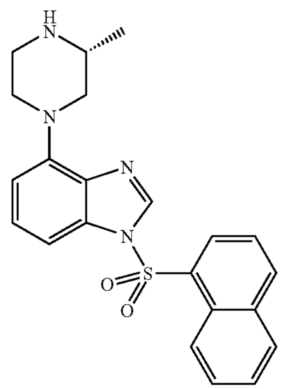 | 4-[(3R)-3-methylpiperazin-1-yl]-1-(naphthalen-1-ylsulfonyl)-1H-benzimidazole | 407.1 | 1.28 |
| 79 | 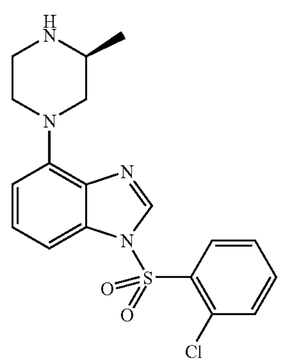 | 1-[(2-chlorophenyl)sulfonyl]-4-[(3S)-3-methylpiperazin-1-yl]-1H-benzimidazole | 391.1 | 0.282 |
| 80 | 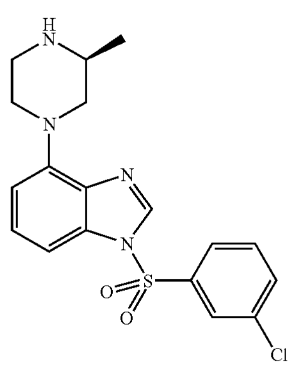 | 1-[(3-chlorophenyl)sulfonyl]-4-[(3S)-3-methylpiperazin-1-yl]-1H-benzimidazole | 391.1 | 0.483 |

TABLE 1-continued

| Ex. | Structure | Name | MS (ES) m/z | 5-HT$_6$ binding Ki (nM) |
|---|---|---|---|---|
| 81 | 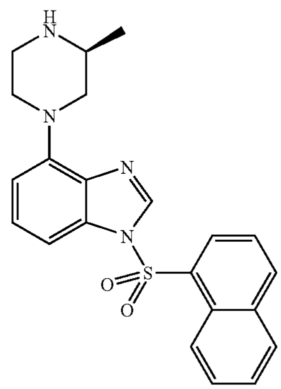 | 4-[(3S)-3-methylpiperazin-1-yl]-1-(naphthalen-1-ylsulfonyl)-1H-benzimidazole | 407.1 | 0.354 |
| 82 | 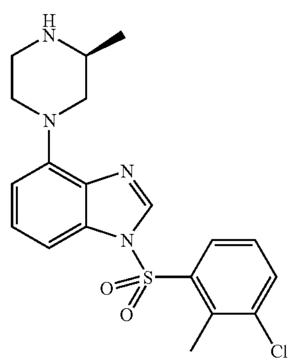 | 1-[(3-chloro-2-methylphenyl)sulfonyl]-4-[(3S)-3-methylpiperazin-1-yl]-1H-benzimidazole | 405.1 | 0.21 |
| 83 | 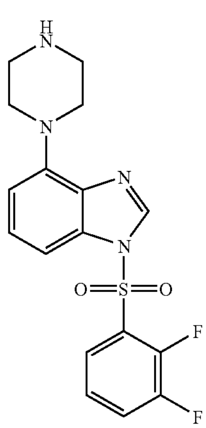 | 1-[(2,3-difluorophenyl)sulfonyl]-4-piperazin-1-yl-1H-benzimidazole | 379.1 | 0.397 |

TABLE 1-continued

| Ex. | Structure | Name | MS (ES) m/z | 5-HT$_6$ binding Ki (nM) |
|---|---|---|---|---|
| 84 | 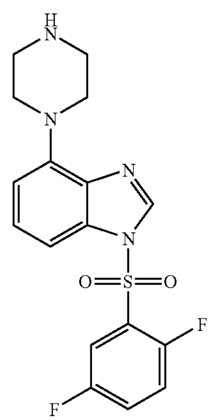 | 1-[(2,5-difluorophenyl)sulfonyl]-4-piperazin-1-yl-1H-benzimidazole | 379.1 | 0.855 |
| 85 | 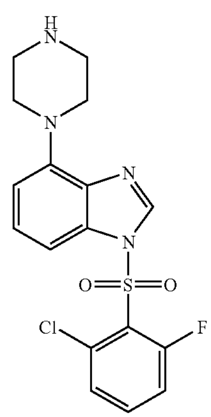 | 1-[(2-chloro-5-fluorophenyl)sulfonyl]-4-piperazin-1-yl-1H-benzimidazole | 395.0 | 0.516 |
| 86 | 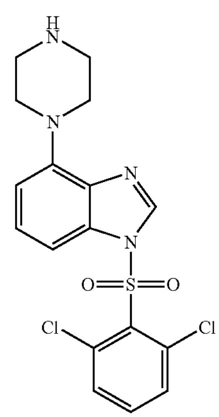 | 1-[(2,6-dichlorophenyl)sulfonyl]-4-piperazin-1-yl-1H-benzimidazole | 411.0 | 1.33 |

TABLE 1-continued

| Ex. | Structure | Name | MS (ES) m/z | 5-HT$_6$ binding Ki (nM) |
|---|---|---|---|---|
| 87 | 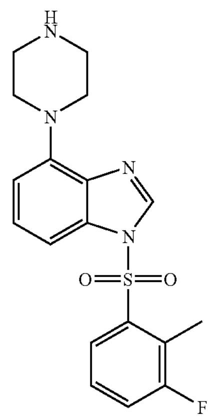 | 1-[(3-fluoro-2-methylphenyl)sulfonyl]-4-piperazin-1-yl-1H-benzimidazole | 375.1 | 0.402 |
| 88 | 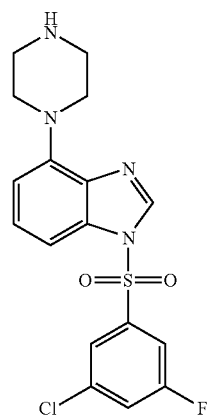 | 1-[(3-chloro-5-fluorophenyl)sulfonyl]-4-piperazin-1-yl-1H-benzimidazole | 395.0 | 0.589 |
| 89 | 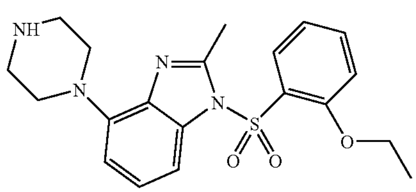 | 1-[(2-ethoxyphenyl)sulfonyl]-2-methyl-4-piperazin-1-yl-1H-benzimidazole | 401.1 | 0.761 |
| 90 | 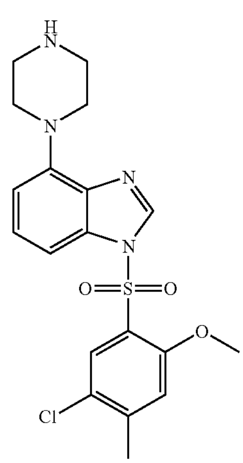 | 1-[(5-chloro-2-methoxy-4-methylphenyl)sulfonyl]-4-piperazin-1-yl-1H-benzimidazole | 421.1 | 12.9 |

TABLE 1-continued

| Ex. | Structure | Name | MS (ES) m/z | 5-HT$_6$ binding Ki (nM) |
|---|---|---|---|---|
| 91 | 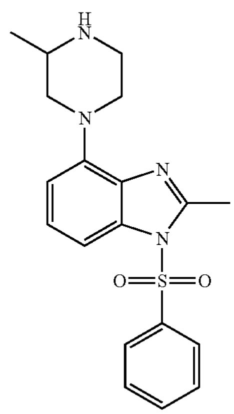 | 2-methyl-4-(3-methylpiperazin-1-yl)-1-(phenylsulfonyl)-1H-benzimidazole | 371.1 | 2.44 |
| 92 | 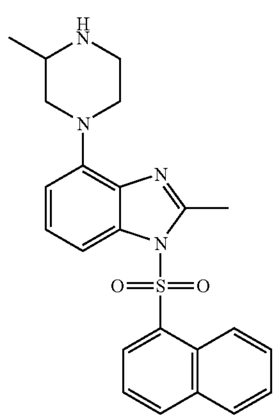 | 2-methyl-4-(3-methylpiperazin-1-yl)-1-(naphthalen-1-ylsulfonyl)-1H-benzimidazole | 421.1 | 0.623 |
| 93 | 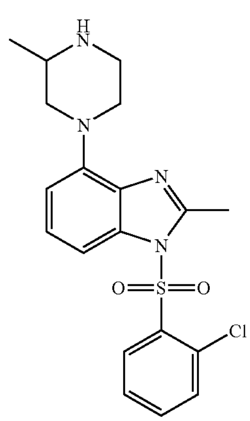 | 1-[(2-chlorophenyl)sulfonyl]-2-methyl-4-(3-methylpiperazin-1-yl)-1H-benzimidazole | 405.1 | 0.488 |

TABLE 1-continued

| Ex. | Structure | Name | MS (ES) m/z | 5-HT₆ binding Ki (nM) |
|---|---|---|---|---|
| 94 | 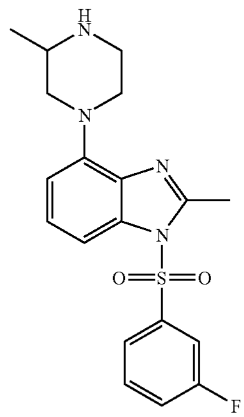 | 1-[(3-fluorophenyl)sulfonyl]-2-methyl-4-(3-methylpiperazin-1-yl)-1H-benzimidazole | 389.1 | 1.07 |
| 95 | 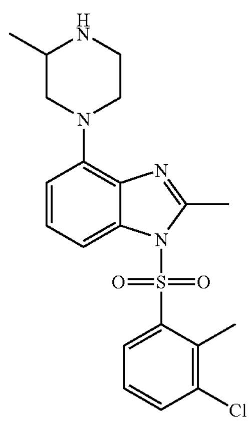 | 1-[(3-chloro-2-methylphenyl)sulfonyl]-2-methyl-4-(3-methylpiperazin-1-yl)-1H-benzimidazole | 419.1 | 0.394 |
| 96 | 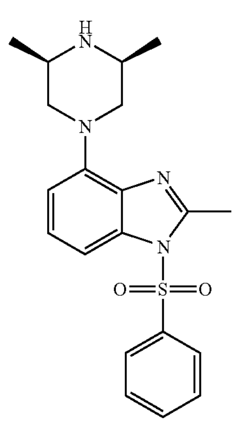 | 4-[(3R,5S)-3,5-dimethylpiperazin-1-yl]-2-methyl-1-(phenylsulfonyl)-1H-benzimidazole | 385.2 | 27.2 |

TABLE 1-continued
| Ex. | Structure | Name | MS (ES) m/z | 5-HT$_6$ binding Ki (nM) |
|---|---|---|---|---|
| 97 | 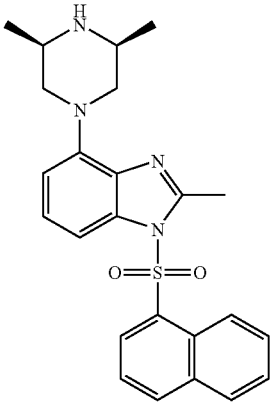 | 4-[(3R,5S)-3,5-dimethylpiperazin-1-yl]-2-methyl-1-(naphthalen-1-ylsulfonyl)-1H-benzimidazole | 435.2 | 3.8 |
| 98 | 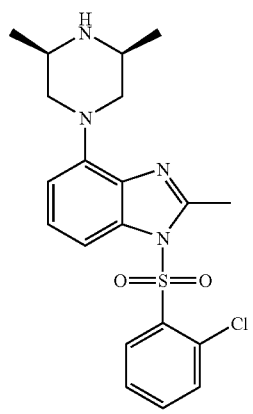 | 1-[(2-chlorophenyl)sulfonyl]-4-[(3R,5S)-3,5-dimethylpiperazin-1-yl]-2-methyl-1H-benzimidazole | 419.1 | 3.5 |
| 99 | 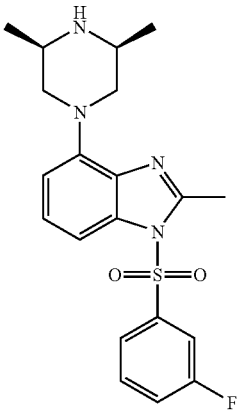 | 4-[(3R,5S)-3,5-dimethylpiperazin-1-yl]-1-[(3-fluorophenyl)sulfonyl]-2-methyl-1H-benzimidazole | 403.1 | 12.9 |

TABLE 1-continued

| Ex. | Structure | Name | MS (ES) m/z | 5-HT$_6$ binding Ki (nM) |
|---|---|---|---|---|
| 100 | 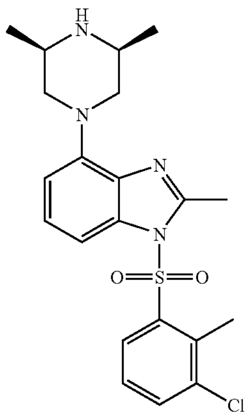 | 1-[(3-chloro-2-methylphenyl)sulfonyl]-4-[(3R,5S)-3,5-dimethylpiperazin-1-yl]-2-methyl-1H-benzimidazole | 433.1 | 2.28 |
| 101 | 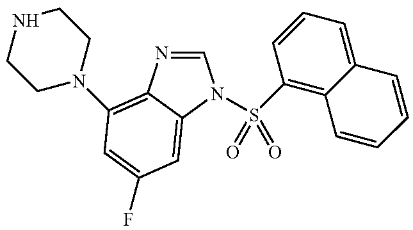 | 6-fluoro-1-(naphthalen-1-ylsulfonyl)-4-piperazin-1-yl-1H-benzimidazole | 411.1 | 1.33 |
| 102 | 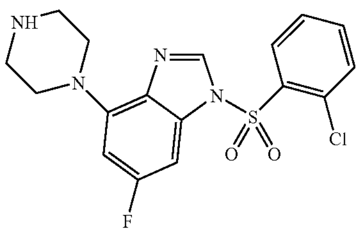 | 1-[(2-chlorophenyl)sulfonyl]-6-fluoro-4-piperazin-1-yl-1H-benzimidazole | 395.0 | 0.698 |
| 103 | 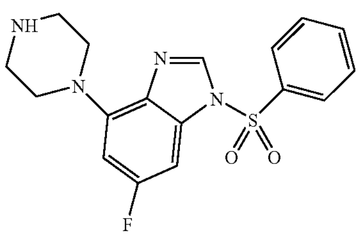 | 6-fluoro-1-(phenylsulfonyl)-4-piperazin-1-yl-1H-benzimidazole | 361.1 | 0.738 |
| 104 | 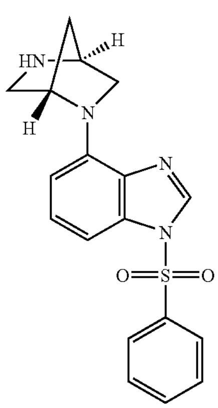 | 4-[(1S,4S)-2,5-diazabicyclo[2.2.1]hept-2-yl]-1-(phenylsulfonyl)-1H-benzimidazole | 355.1 | 44.7 |

TABLE 1-continued

| Ex. | Structure | Name | MS (ES) m/z | 5-HT$_6$ binding Ki (nM) |
|---|---|---|---|---|
| 105 | 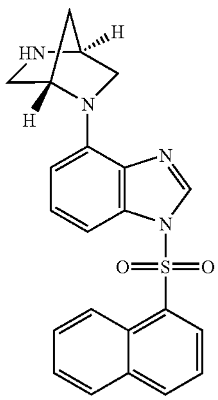 | 4-[(1S,4S)-2,5-diazabicyclo[2.2.1]hept-2-yl]-1-(naphthalen-1-ylsulfonyl)-1H-benzimidazole | 405.1 | 7.55 |
| 106 | 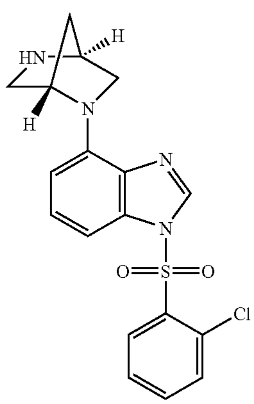 | 1-[(2-chlorophenyl)sulfonyl]-4-[(1S,4S)-2,5-diazabicyclo[2.2.1]hept-2-yl]-1H-benzimidazole | 389.0 | 5.3 |
| 107 | 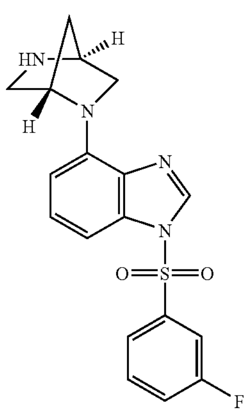 | 4-[(1S,4S)-2,5-diazabicyclo[2.2.1]hept-2-yl]-1-[(3-fluorophenyl)sulfonyl]-1H-benzimidazole | 373.1 | 22.1 |

TABLE 1-continued

| Ex. | Structure | Name | MS (ES) m/z | 5-HT$_6$ binding Ki (nM) |
|---|---|---|---|---|
| 108 | 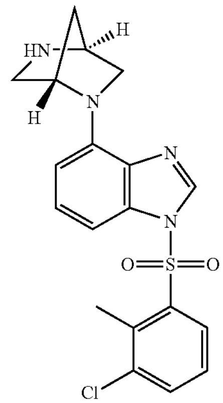 | 1-[(3-chloro-2-methylphenyl)sulfonyl]-4-[(1S,4S)-2,5-diazabicyclo[2.2.1]hept-2-yl]-1H-benzimidazole | 403.1 | 2.86 |
| 109 | 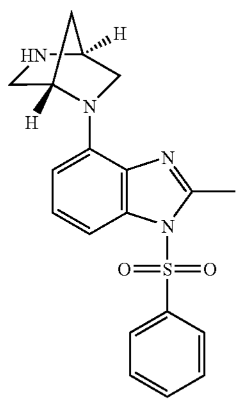 | 4-[(1S,4S)-2,5-diazabicyclo[2.2.1]hept-2-yl]-2-methyl-1-(phenylsulfonyl)-1H-benzimidazole | 369.1 | 30.5 |
| 110 | 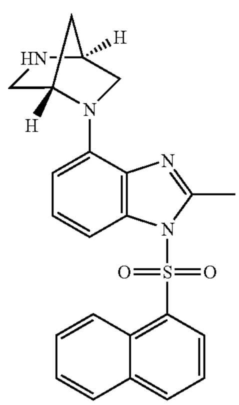 | 4-[(1S,4S)-2,5-diazabicyclo[2.2.1]hept-2-yl]-2-methyl-1-(naphthalen-1-ylsulfonyl)-1H-benzimidazole | 419.1 | 9.92 |

TABLE 1-continued

| Ex. | Structure | Name | MS (ES) m/z | 5-HT$_6$ binding Ki (nM) |
|---|---|---|---|---|
| 111 | 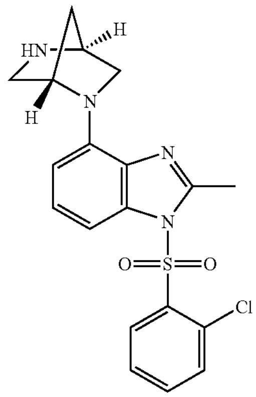 | 1-[(2-chlorophenyl)sulfonyl]-4-[(1S,4S)-2,5-diazabicyclo[2.2.1]hept-2-yl]-2-methyl-1H-benzimidazole | 403.0 | 21 |
| 112 | 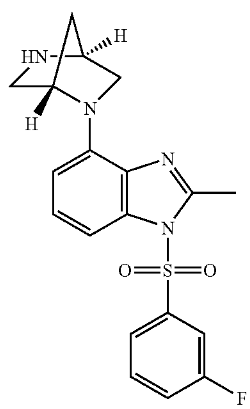 | 4-[(1S,4S)-2,5-diazabicyclo[2.2.1]hept-2-yl]-1-[(3-fluorophenyl)sulfonyl]-2-methyl-1H-benzimidazole | 387.1 | 39.9 |
| 113 | 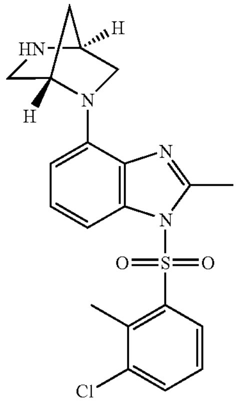 | 1-[(3-chloro-2-methylphenyl)sulfonyl]-4-[(1S,4S)-2,5-diazabicyclo[2.2.1]hept-2-yl]-2-methyl-1H-benzimidazole | 417.1 | 14.1 |

TABLE 1-continued

| Ex. | Structure | Name | MS (ES) m/z | 5-HT$_6$ binding Ki (nM) |
|---|---|---|---|---|
| 114 | 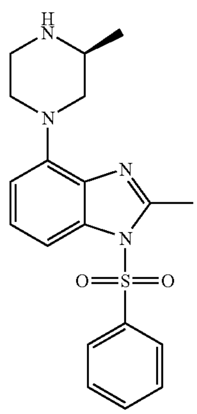 | 2-methyl-4-[(3R)-3-methylpiperazin-1-yl]-1-(phenylsulfonyl)-1H-benzimidazole | 393.1 | 3.17 |
| 115 | 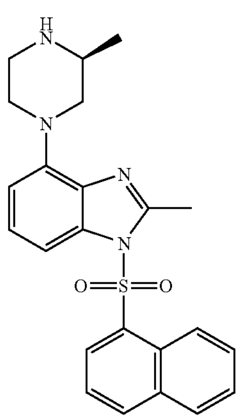 | 2-methyl-4-[(3R)-3-methylpiperazin-1-yl]-1-(1-naphthylsulfonyl)-1H-benzimidazole | 421.1 | 1.12 |
| 116 | 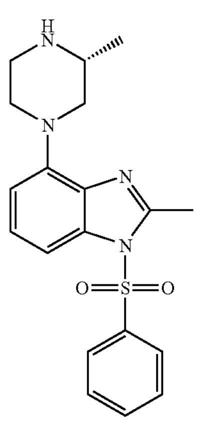 | 2-methyl-4-[(3S)-3-methylpiperazin-1-yl]-1-(phenylsulfonyl)-1H-benzimidazole | 371.1 | 0.951 |

TABLE 1-continued

| Ex. | Structure | Name | MS (ES) m/z | 5-HT$_6$ binding Ki (nM) |
|---|---|---|---|---|
| 117 | 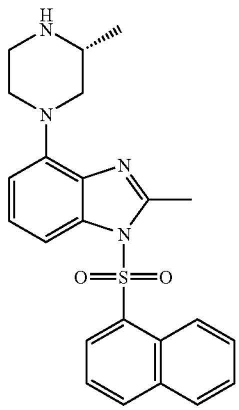 | 2-methyl-4-[(3S)-3-methylpiperazin-1-yl]-1-(1-naphthylsulfonyl)-1H-benzimidazole | 421.1 | 0.305 |
| 118 | 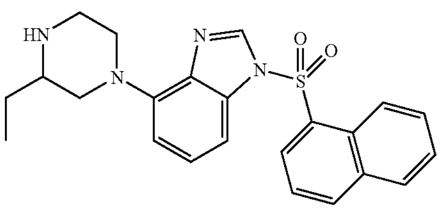 | 4-(3-ethylpiperazin-1-yl)-1-(1-naphthylsulfonyl)-1H-benzimidazole | 421.1 | 1.38 |
| 119 | 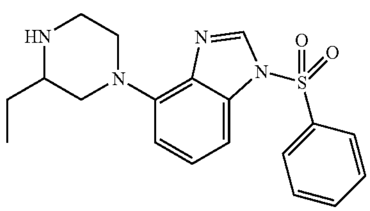 | 4-(3-ethylpiperazin-1-yl)-1-(phenylsulfonyl)-1H-benzimidazole | 371.1 | 0.484 |
| 120 | 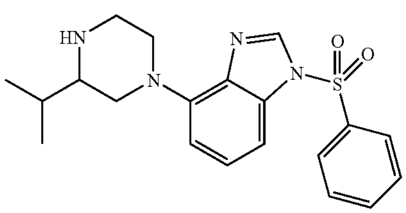 | 4-(3-isopropylpiperazin-1-yl)-1-(phenylsulfonyl)-1H-benzimidazole | 385.1 | 6.11 |
| 121 | 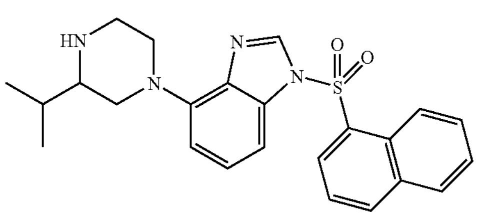 | 4-(3-isopropylpiperazin-1-yl)-1-(1-naphthylsulfonyl)-1H-benzimidazole | 435.1 | 0.952 |
| 122 | 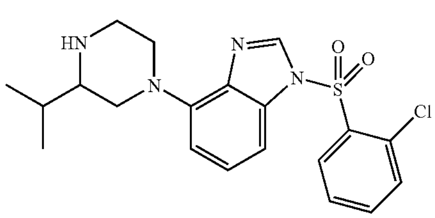 | 1-[(2-chlorophenyl)sulfonyl]-4-(3-isopropylpiperazin-1-yl)-1H-benzimidazole | 419.1 | 1.08 |

TABLE 1-continued

| Ex. | Structure | Name | MS (ES) m/z | 5-HT$_6$ binding Ki (nM) |
|---|---|---|---|---|
| 123 | 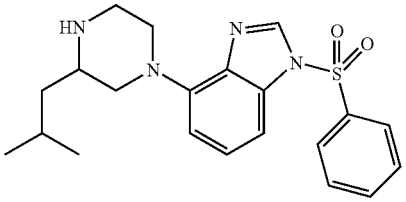 | 4-(3-isobutylpiperazin-1-yl)-1-(phenylsulfonyl)-1H-benzimidazole | 399.2 | 34.3 |
| 124 | 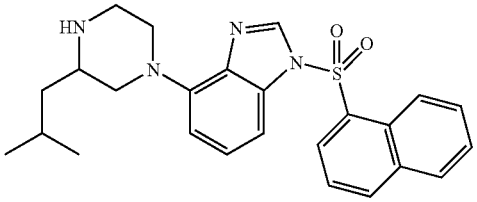 | 4-(3-isobutylpiperazin-1-yl)-1-(1-naphthylsulfonyl)-1H-benzimidazole | 449.1 | 8.32 |
| 125 | 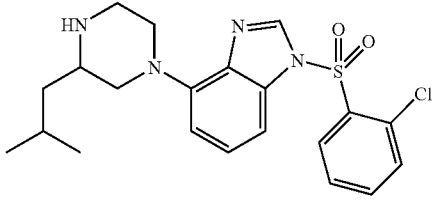 | 1-[(2-chlorophenyl)sulfonyl]-4-(3-isobutylpiperazin-1-yl)-1H-benzimidazole | 433.1 | 4.98 |
| 126 | 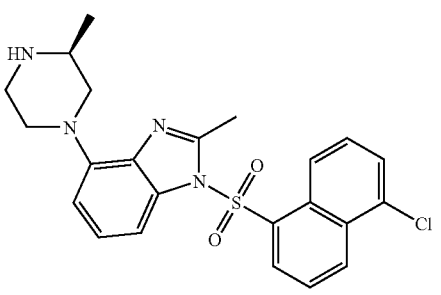 | 1-[(5-chloro-1-naphthyl)sulfonyl]-2-methyl-4-[(3S)-3-methylpiperazin-1-yl]-1H-benzimidazole | 455.1 | 1.05 |
| 127 | 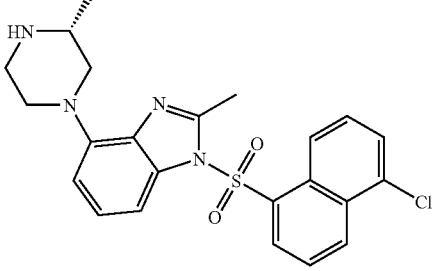 | 1-[(5-chloro-1-naphthyl)sulfonyl]-2-methyl-4-[(3R)-3-methylpiperazin-1-yl]-1H-benzimidazole | 455.1 | 8.38 |

TABLE 1-continued

| Ex. | Structure | Name | MS (ES) m/z | 5-HT$_6$ binding Ki (nM) |
|---|---|---|---|---|
| 128 | 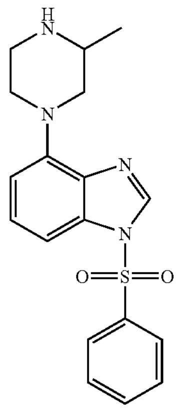 | 4-(3-methylpiperazin-1-yl)-1-(phenylsulfonyl)-1H-benzimidazole | 357.1 | 0.931 |
| 129 | 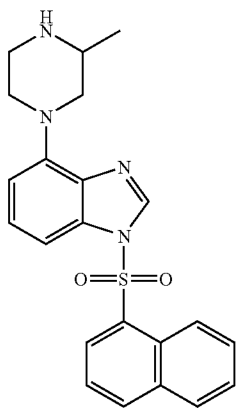 | 4-(3-methylpiperazin-1-yl)-1-(1-naphthylsulfonyl)-1H-benzimidazole | 407.1 | 0.051 |

Throughout this application, various publications are referenced. The disclosures of these publications in their entireties are hereby incorporated by reference into this application in order to more fully describe the state of the art as known to those skilled therein as of the date of the invention described and claimed herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A compound that is 2-methyl-1-(phenylsulfonyl)-4-piperazin-1-yl-1H-benzimidazole or a pharmaceutically acceptable salt thereof.

2. A composition comprising the compound of claim 1 and a pharmaceutically acceptable carrier.

3. The composition of claim 2, wherein the pharmaceutically acceptable carrier is suitable for oral administration and the composition comprises an oral dosage form.

4. A method of treating a 5-HT$_6$-related disorder, in a mammal, which the method comprises administering to the mammal in need thereof the compound of claim 1 in an amount effective to treat the 5-HT$_6$-related disorder, wherein the 5-HT$_6$-related disorder is selected from depression, obesity, cognitive impairment associated with schizophrenia, cognitive dysfunction associated with Alzheimer's disease, and schizophrenia.

5. The method of claim 4, wherein the 5-HT$_6$-related disorder is cognitive impairment associated with schizophrenia.

6. The compound of claim 1, wherein the compound is 2-methyl-1-(phenylsulfonyl)-4-piperazin-1-yl-1H-benzimidazole.

7. A composition comprising the compound of claim 6 and a pharmaceutically acceptable carrier.

8. The composition of claim 7, wherein the pharmaceutically acceptable carrier is suitable for oral administration and the composition comprises an oral dosage form.

9. A method of treating a 5-HT$_6$-related disorder, in a mammal, which the method comprises administering to the mammal in need thereof the compound of claim 6 in an amount effective to treat the 5-HT$_6$-related disorder, wherein the 5-HT$_6$-related disorder is selected from depression, obesity, cognitive impairment associated with schizophrenia, cognitive dysfunction associated with Alzheimer's disease, and schizophrenia.

10. The method of claim 9, wherein the 5-HT$_6$-related disorder is cognitive impairment associated with schizophrenia.

11. The method of claim 4, wherein the 5-HT$_6$-related disorder is cognitive dysfunction associated with Alzheimer's disease.

12. The method of claim 9, wherein the 5-$HT_6$-related disorder is cognitive dysfunction associated with Alzheimer's disease.

13. The compound of claim 1, wherein the compound is 2-methyl-1-(phenylsulfonyl)-4-piperazin-1-yl-1H-benzimidazole succinate.

14. A composition comprising the compound of claim 13 and a pharmaceutically acceptable carrier.

15. The composition of claim 14, wherein the pharmaceutically acceptable carrier is suitable for oral administration and the composition comprises an oral dosage form.

16. A method of treating a 5-$HT_6$-related disorder, in a mammal, which the method comprises administering to the mammal in need thereof the compound of claim 13 in an amount effective to treat the 5-$HT_6$-related disorder, wherein the 5-$HT_6$-related disorder is selected from depression, obesity, cognitive impairment associated with schizophrenia, cognitive dysfunction associated with Alzheimer's disease, and schizophrenia.

17. The method of claim 16, wherein the 5-$HT_6$-related disorder is cognitive impairment associated with schizophrenia.

18. The method of claim 16, wherein the 5-$HT_6$-related disorder is cognitive dysfunction associated with Alzheimer's disease.

\* \* \* \* \*